(12) United States Patent
Liu

(10) Patent No.: US 9,925,138 B2
(45) Date of Patent: Mar. 27, 2018

(54) STABLE SOLID FINGOLIMOD DOSAGE FORMS

(71) Applicant: Handa Pharmaceuticals, LLC, Fremont, CA (US)

(72) Inventor: Fangyu Liu, Saratoga, CA (US)

(73) Assignee: Handa Pharmaceuticals, LLC, Fremont, CA (US)

( * ) Notice: Subject to any disclaimer, the term of this patent is extended or adjusted under 35 U.S.C. 154(b) by 0 days.

(21) Appl. No.: 15/084,226

(22) Filed: Mar. 29, 2016

(65) Prior Publication Data

US 2016/0206557 A1 Jul. 21, 2016

Related U.S. Application Data

(63) Continuation of application No. PCT/US2016/013938, filed on Jan. 19, 2016.

(60) Provisional application No. 62/216,100, filed on Sep. 9, 2015, provisional application No. 62/105,603, filed on Jan. 20, 2015.

(51) Int. Cl.
*A61K 9/52* (2006.01)
*A61K 9/00* (2006.01)
*A61K 31/138* (2006.01)
*A61K 9/20* (2006.01)

(52) U.S. Cl.
CPC ............ *A61K 9/0056* (2013.01); *A61K 9/006* (2013.01); *A61K 9/2004* (2013.01); *A61K 31/138* (2013.01)

(58) Field of Classification Search
CPC .......... A61K 9/145; A61K 9/14; A61K 9/141; A61K 9/143; A61K 9/148; A61K 9/16; A61K 9/1605; A61K 9/20; A61K 9/2004; A61K 9/2009; A61K 9/2018; A61K 9/2027; A61K 9/205; A61K 9/2054; A61K 9/259
See application file for complete search history.

(56) References Cited

U.S. PATENT DOCUMENTS

| | | |
|---|---|---|
| 4,136,145 A | 1/1979 | Fuchs et al. |
| 4,305,502 A | 12/1981 | Gregory et al. |
| 4,371,516 A | 2/1983 | Gregory et al. |
| 4,760,093 A | 7/1988 | Blank et al. |
| 4,760,094 A | 7/1988 | Blank et al. |
| 4,767,789 A | 8/1988 | Blank et al. |
| 4,855,326 A | 8/1989 | Fuisz |
| 5,178,878 A | 1/1993 | Wehling et al. |
| 5,298,261 A | 3/1994 | Pebley et al. |
| 5,464,632 A | 11/1995 | Cousin et al. |
| 5,503,846 A | 4/1996 | Wehling et al. |
| 5,576,014 A | 11/1996 | Mizumoto et al. |
| 5,587,180 A | 12/1996 | Allen et al. |
| 5,604,229 A | 2/1997 | Fujita et al. |
| 5,720,974 A | 2/1998 | Makino et al. |
| 5,807,576 A | 9/1998 | Allen et al. |
| 5,851,553 A | 12/1998 | Myers et al. |
| 5,866,163 A | 2/1999 | Myers et al. |
| 5,869,098 A | 2/1999 | Misra et al. |
| 5,876,759 A | 3/1999 | Gowan, Jr. |
| 6,004,565 A | 12/1999 | Chiba et al. |
| 6,010,719 A | 1/2000 | Remon et al. |
| 6,024,981 A | 2/2000 | Khankari et al. |
| 6,027,746 A | 2/2000 | Lech |
| 6,048,541 A | 4/2000 | Misra et al. |
| 6,106,861 A | 8/2000 | Chauveau et al. |
| 6,149,938 A | 11/2000 | Bonadeo et al. |
| 6,200,604 B1 | 3/2001 | Pather et al. |
| 6,221,392 B1 | 4/2001 | Khankari et al. |
| 6,264,981 B1 | 7/2001 | Zhang et al. |
| 6,316,029 B1 | 11/2001 | Jain et al. |
| 6,465,009 B1 | 10/2002 | Liu et al. |
| 6,740,341 B1 | 5/2004 | Holt et al. |
| 7,399,485 B1 | 7/2008 | Shimizu et al. |
| 8,017,150 B2 | 9/2011 | Yang et al. |
| 8,119,158 B2 | 2/2012 | Moe et al. |
| 8,324,283 B2 | 12/2012 | Oomura et al. |
| 8,454,996 B2 | 6/2013 | Pettersson et al. |
| 8,470,361 B2 | 6/2013 | Pettersson |
| 8,530,522 B2 | 9/2013 | Jordine et al. |
| 8,673,918 B2 | 3/2014 | Ruegger et al. |
| 8,735,627 B2 | 5/2014 | Marom et al. |
| 8,766,005 B2 | 7/2014 | Gidwani et al. |
| 9,186,333 B2 | 11/2015 | Hrakovsky |
| 2006/0275357 A1 | 12/2006 | Oomura et al. |
| 2008/0311188 A1 | 12/2008 | Oomura et al. |
| 2009/0203798 A1 | 8/2009 | Oomura et al. |

(Continued)

FOREIGN PATENT DOCUMENTS

| | | |
|---|---|---|
| EP | 1050301 | 1/1999 |
| EP | 0812588 | 12/1999 |

(Continued)

OTHER PUBLICATIONS

United States Pharmacopeia, The Official Compendia of Standards, 38th Ed. (2015), Section 1217, p. 1433-1435.
United States Pharmacopeia, The Official Compendia of Standards, 36th Ed. (2013), Sections 701, 711, Disintegration, Dissolution, p. 305-307.
Chowhan, Z. T., Effect of Moisture and Crushing Strength on Tablet Friability and in Vitro Dissolution, J. of Pharm. Sci. 71:1371-1375 (1982).
Martindale, The Extra Pharmacopoeia, The Pharmaceutical Press, 29th Ed. (1989), pp. 1243-1249.
Remington, The Science and Practice of Pharmacy, vol. 1, Pharmaceutical Press, 22nd Ed. (2013), pp. 791-792.

(Continued)

*Primary Examiner* — Micah Paul Young
(74) *Attorney, Agent, or Firm* — Florek & Endres PLLC

(57) ABSTRACT

The present invention relates to a solid pharmaceutical dosage forms and methods for preparing the solid pharmaceutical dosage form that contains fingolimod or its pharmaceutically acceptable salts, conjugates or complexes thereof. The solid pharmaceutical dosage forms may rapidly disintegrates in a patient's oral cavity.

18 Claims, No Drawings

(56) References Cited

U.S. PATENT DOCUMENTS

| | | |
|---|---|---|
| 2010/0040678 A1 | 2/2010 | Ambuhl et al. |
| 2011/0105620 A1 | 5/2011 | Oomura et al. |
| 2011/0281912 A1 | 11/2011 | Winter et al. |
| 2012/0004067 A1 | 1/2012 | Aota et al. |
| 2012/0184617 A1 | 7/2012 | Gidwani et al. |
| 2013/0034603 A1* | 2/2013 | Hrakovsky ............ A61K 9/145 424/456 |
| 2013/0095177 A1 | 4/2013 | Paetz et al. |
| 2013/0102682 A1 | 4/2013 | Paetz et al. |
| 2013/0102683 A1 | 4/2013 | Paetz et al. |
| 2013/0281739 A1 | 10/2013 | Shrawat et al. |
| 2013/0308675 A1 | 11/2013 | Sneed et al. |
| 2014/0051766 A1 | 2/2014 | Jordine et al. |
| 2014/0199382 A1* | 7/2014 | Kulkarni ............ A61K 9/4866 424/451 |
| 2014/0227358 A1 | 8/2014 | Ambuhl et al. |
| 2014/0235895 A1 | 8/2014 | Katkam et al. |
| 2014/0255497 A1 | 9/2014 | Oomura et al. |
| 2014/0371323 A1 | 12/2014 | Rane |
| 2015/0165046 A1 | 6/2015 | Ruegger et al. |

FOREIGN PATENT DOCUMENTS

| | | |
|---|---|---|
| WO | 2004/089341 | 10/2004 |
| WO | 2008/015695 | 5/2008 |
| WO | 2009/048993 | 5/2010 |
| WO | 2010/055028 | 5/2010 |
| WO | 2010/055027 | 8/2010 |

OTHER PUBLICATIONS

Remington, The Science and Practice of Pharmacy, vol. 1, Pharmaceutical Press, 22nd Ed. (2013), pp. 956-957.
Remington, The Science and Practice of Pharmacy, vol. 1, Pharmaceutical Press, 22nd Ed. (2013), pp. 891-894.
Remington, The Science and Practice of Pharmacy, Lippincott Williams & Wilkins, 21st Ed. (2005). pp. 706-711.
FDA's Guidance for Industry Bioavailability and Bioequivalence Studies for Orally Administered Drug Products—General Considerations, Mar. 2003.
FDA's Guidance for Industry Statistical Approaches to Establishing Bioequivalence, Jan. 2001.
United States Pharmacopeia, The Official Compendia of Standards, 38th Ed. (2006), Section 1216, Friability, p. 1432.
Agnès Wittmann-Regis, International Preliminary Report on Patentability in PCT/US2016/013938, dated Jul. 25, 2017, The International Bureau of WIPO, Geneva, Switzerland.

* cited by examiner

STABLE SOLID FINGOLIMOD DOSAGE FORMS

This application is a continuation of International Patent Application No. PCT/US2016/013938 filed on Jan. 19, 2016 and claims the benefits of U.S. Provisional Patent Application No. 62/105,603 filed on Jan. 20, 2015 and U.S. Provisional Patent Application No. 62/216,100 filed on Sep. 9, 2015 which are incorporated herein by reference.

FIELD OF THE INVENTION

The present invention relates to pharmaceutical dosage forms and methods for preparing pharmaceutical dosage forms containing fingolimod and pharmaceutically acceptable salts, conjugates, or complexes thereof, such as the hydrochloride salt. The pharmaceutical dosage forms of the present invention should be stable upon storage. Embodiments of the present invention should rapidly disintegrate or dissolve in the oral cavity of the patient. The present invention also relates to novel fingolimod salts, conjugates or complexes which can be incorporated into pharmaceutical dosage forms.

BACKGROUND

Pharmaceutically active agents are commonly formulated as solid tablets for oral administration due to reasons of stability, economy, simplicity and convenience of dosing. However, many patients cannot or will not accept tablet administration. Infants, children, individuals suffering from certain injuries or illnesses, and many elderly and disabled individuals cannot swallow or chew sufficiently to effectively administer a pharmaceutically active agent by means of a solid tablet. An effective means for oral administration of pharmaceutically active agents to these individuals would be highly beneficial. While liquid formulations can address this need in some cases, the technical complexities of liquid formulations and difficulties in patient compliance and ease of administration make liquid formulations a less than optimal approach. Thus, there is a great need to develop solid oral tablets which can be administered to this patient population. In these individuals, if a solid tablet is used to administer a pharmaceutically active agent, the ability of that preparation to rapidly disintegrate upon contact with the oral cavity, such as the tongue, buccal cavity or sublingual area of the mouth, and to deliver a therapeutically effective dose of the drug would be a major advantage. Furthermore, in many circumstances, it is important to have a fast disintegrating tablet so that the pharmaceutically active ingredient is absorbed as rapidly as possible.

Many different rapidly disintegrating oral dosage forms are described in the art. Some rapidly disintegrating oral dosage forms are described in U.S. Pat. Nos. 4,136,145; 4,371,516; 4,760,093; 4,767,789; 4,855,326; 5,178,878; 5,298,261; 5,464,632; 5,576,014; 5,587,180; 5,720,974; 5,807,576; 5,587,180; 5,866,163; 5,869,098; 6,010,719; 6,024,981; 6,048,541; 6,149,938; 6,200,604; 6,316,029; 6,465,009; 8,017,150; 8,119,158; 8,454,996; and 8,470,361, which are incorporated herein by reference. These prior art rapidly disintegrating oral dosage forms employ a variety of techniques to facilitate the rapid disintegration of the dosage forms. For example, U.S. Pat. Nos. 4,136,145 and 8,017,150 describe preparation of thin films; U.S. Pat. Nos. 4,371,516 and 6,010,719 describe preparation of dosage forms that employ a lyophilization step; U.S. Pat. Nos. 6,200,604 and 8,119,158 describe the use of effervescent couples; U.S. Pat. Nos. 5,178,878 and 6,264,981 describe the use of large quantities of highly water soluble sugar alcohols; U.S. Pat. Nos. 5,576,014 and 6,465,009 describe the use of a mixture of high and low moldable sugars; U.S. Pat. Nos. 8,454,996 and 8,470,361 describe the use of disintegrants with ordered mixtures of drug and carrier particles; U.S. Pat. No. 5,298,261 describes the use of vacuum drying; and U.S. Pat. No. 5,587,180 describes the use of spray drying to create a support matrix.

Fingolimod is a sphingosine-1 phosphate (SIP) receptor agonist, or modulator, with immunosuppressive activity. Fingolimod, in the form of its hydrochloride salt, is also known as 2-amino-2-[2-(4-octylphenyl)ethyl]propan-1,3-diol hydrochloride, and has the following structure:

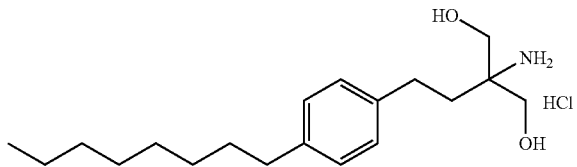 [SMILES: CCCCCCCCc1ccc(CCC(N)(CO)CO)cc1 ; Cl]

Fingolimod was approved in 2010 and is currently marketed in the United States under the tradename GILENYA as an immediate release capsule for the treatment of multiple sclerosis. This formulation contains 0.5 mg equivalent of fingolimod base in the form of the hydrochloride salt. The fingolimod compound and methods for its synthesis and use are described U.S. Pat. No. 5,604,229.

Fingolimod contains a primary amine and is known to be susceptible to a Maillard reaction in the presence of reducing sugars. Efforts to prevent this degradation reaction and prepare stable formulations of fingolimod are described in U.S. Pat. No. 8,673,918 and U.S. Published Application Nos. 2006/0275357, 2010/0040678, and 2013/0034603. The aforementioned patent and patent publications teach the use of sugar alcohols to prevent the Maillard reaction and suggest that one of the potential fingolimod dosage forms could be tablets designed to rapidly disintegrating in the oral cavity of a patient.

To date, there is no technology specifically designed to provide a dosage form containing fingolimod or pharmaceutically acceptable salts, conjugates or complexes thereof that rapidly dissolves in a patient's oral cavity, stable upon storage, easy to manufacture, and exhibits a low friability.

These and other objectives are met by the present invention.

SUMMARY OF THE INVENTION

The present invention is a stable pharmaceutically acceptable solid oral dosage form comprising fingolimod or a pharmaceutically acceptable salt, conjugate or complex thereof. Embodiments of the present invention include but are not limited to a pharmaceutically acceptable solid dosage form containing fingolimod or a pharmaceutically acceptable salt, conjugate or complex thereof that rapidly dissolves when placed in a patient's oral cavity. The present invention also includes methods for producing the pharmaceutically acceptable solid oral dosage forms containing fingolimod or a pharmaceutically acceptable salt, conjugate or complex thereof.

The pharmaceutically acceptable solid dosage forms of the present invention comprise fingolimod or a pharmaceutically acceptable salt, conjugate or complex thereof and at least one sugar alcohol. In certain embodiments the pharmaceutically acceptable solid dosage forms of the present invention comprise fingolimod or a pharmaceutically acceptable salt, conjugate, or complex thereof and a combination at least one sugar alcohol and a moisture facilitating compound (hereinafter "MFC"). The sugar alcohol may be any commonly known sugar alcohol, preferably a crystalline sugar alcohol that does not easily convert from a crystalline form to an amorphous form (hereinafter "a NCF sugar alcohol"). The MFC is a hygroscopic compound that readily attracts and/or absorbs moisture from the surrounding air or is a sugar alcohol that easily converts to an amorphous form (hereinafter "a CAF sugar alcohol"). In preferred embodiments the CAF sugar alcohol when present in the solid dosage form is preferably in an amorphous form in the solid dosage form and the NCF sugar alcohol when present in the solid dosage form is preferably in a crystalline form in the solid dosage form.

The pharmaceutically acceptable solid dosage forms of the present invention may further comprise conventional pharmaceutically acceptable excipients such as lubricants, fillers, binders, disintegrants, glidants, solubilizing agents, flavoring agents, gas producing agents, pH adjusting agents, antioxidants, chelating agents, or mixtures of the foregoing.

The pharmaceutically acceptable solid dosage forms of the present invention may be prepared by any method known in the pharmaceutical arts such wet granulation, slugging and/or dry mixing the fingolimod with the selected excipients and forming the granules, aggregates or mixtures into tablets.

In certain embodiments of the present invention, the pharmaceutically solid dosage forms of the present invention are in the form of a tablet, pellet, or granule and exhibits a friability of less than 2%, preferably less than 1.5%, and most preferably less than 1.0%.

In certain embodiments of the present invention, the pharmaceutically acceptable solid dosage forms of the present invention should dissolve in a patient's oral cavity or in a United States Pharmacopeia (USP) Disintegration test in less than 2.5 minutes, preferably less than 2.0 minutes, and most preferably less than 1.5 minutes.

In certain embodiments of the present invention, the pharmaceutically acceptable solid dosage forms are a tablet comprising one or more scored, indented or demassed area that allows the tablets to be divided into portions such as half, thirds or quarters which in turn allows a patient to administer a divided dose.

In certain embodiments of the present invention, the pharmaceutically acceptable solid dosage forms of the present invention can be prepared by dissolving or suspending the fingolimod or a pharmaceutically acceptable salt thereof in a suitable solvent along with at least one or more pharmaceutically acceptable excipients. In certain embodiments, the fingolimod is dissolved with at least one solubilizing agent, preferably an anionic surfactant. The resulting fingolimod solution or suspension is sprayed onto or mixed with additional pharmaceutically acceptable excipients such as a sugar alcohol to prepare fingolimod granules that may be further processed into a tablet or pellet, or the granules may be packaged into a unit dose for administration to a patient.

In another embodiment of the present invention, the pharmaceutically acceptable solid dosage forms of the present invention can be prepared by dry mixing the fingolimod with at least one pharmaceutically acceptable excipient such as a sugar alcohol. In certain embodiments the fingolimod is dry mixed with at least one sugar alcohol and at least one antioxidant. The dry mixture is formed into granules with the aid of a granulating solution or suspension which comprises a suitable solvent and optionally at least one additional pharmaceutically acceptable solvent. The resulting granules may be further processed into a tablet or pellet, or the granules may be packaged into a unit dose for administration to a patient.

In an alternative embodiment, the pharmaceutically acceptable solid dosage forms of the present invention can be prepared by dissolving or suspending the fingolimod or a pharmaceutically acceptable salt thereof in a suitable solvent along with at least a portion of the MFC, preferably a CAF sugar alcohol and optionally one solubilizing agent, to form a drug/MFC liquid composition and drying the resulting drug/MFC liquid composition to create a matrix comprising the fingolimod or pharmaceutically acceptable salt, conjugate or complex thereof and a MFC. The drying can be conducted by any method known in the pharmaceutical arts including but not limited to spray drying, freeze drying (sometimes referred to as lyophilization), vacuum drying or conventional oven drying. A sugar alcohol, preferably an NCF sugar alcohol, or a portion thereof, may be added to the drug/MFC liquid composition prior to drying. Alternatively, a sugar alcohol, preferably an NCF sugar alcohol, or a portion thereof, may be combined with the drug/MFC liquid composition during the drying process, i.e., as a substrate during the spray drying, or a sugar alcohol or a portion thereof may be combined with the dried matrix comprising the fingolimod or pharmaceutically acceptable salt, conjugate or complex and the MFC. Similarly, one or more of the additional pharmaceutically acceptable excipient(s) such as fillers, binders, disintegrants, glidants, solubilizing agents, flavoring agents, pH adjusting agents, antioxidants, chelating agents or mixtures of the foregoing may also be added to the drug/sugar alcohol liquid composition prior to drying. The additional pharmaceutically acceptable excipient(s) may also be added during the drying step, such as a substrate during a spray drying and/or added to the dried matrix comprising the fingolimod or pharmaceutically acceptable salt, conjugate or complex and the MFC. The matrix may be further mixed with a lubricant, and formed into a tablet, pellet, or granule.

In certain embodiments of the present invention, the pharmaceutically acceptable solid dosage forms of the present invention can be prepared by dry mixing the fingolimod with one or more pharmaceutically acceptable excipients and compressing the mixture into a tablet. Alternatively, the fingolimod may be dry mixed with one or more pharmaceutically acceptable excipients, preferably including an antioxidant, and the dry mix, compacted with an appropriate device such as a roller compactor or a tablet press, and the resulting compacted material is milled and sized to create fingolimod aggregates of desired size. The fingolimod aggregates may be mixed with additional pharmaceutically acceptable excipients such as a lubricant and then pressed into a tablet.

Once the pharmaceutically acceptable solid dosage forms of the present invention, i.e., tablet, pellet, or granule, are formed by any of the methods described above, they may be humidified for a period of time by exposing the dosage form to an environment of at least about 50% to about 100% relative humidity, preferably about 55% to about 95% relative humidity, and most preferably about 60% to about 90% relative humidity. After humidifying the dosage form, it is dried until a hardness of about 10 newtons to about 350 newtons, preferably about 15 newtons to about 250 newtons, and most preferably about 20 newtons to about 150 newtons, is obtained.

The period of time for the humidifying step is about 15 minutes to about 40 hours, preferably about 1 hour to about 24 hours, and mostly preferably about 1 hour to about 12 hours. The time period will vary depending upon the relative humidity and temperature of the humidifying step. The period of time for the drying step can vary from about 0.5 hours to about 40 hours, depending upon the temperature and relative humidity of the drying apparatus. This embodiment of the present invention allows the resulting tablets, pellets, or granules to be stored in bulk containers such as polyethylene bags and/or drums for a period of time without significant degradation or breaking. After bulk storage, the solid dosage form may be packaged in bottles or conventional blister packs without significant breaking or destruction.

Following administration of the pharmaceutically acceptable solid dosage forms of certain embodiments of the present invention to a patient, the dosage from should be held in the patient's mouth or buccal cavity until it dissolves. The patient may swallow the remnants of the dissolved dosage form. Following a single dose administration of the pharmaceutically acceptable solid dosage form of the present invention to healthy subjects under fasting conditions, the subjects should exhibit a time to maximum fingolimod concentration ($T_{max}$) of about 8 hours to about 40 hours, preferably about 10 hours to about 35 hours and most preferably about 12 to about 30 hours, a dose adjusted maximum fingolimod concentration ($C_{max/dose}$) of about 0.50 ng/ml/mg to about 2.0 ng/ml/mg, preferably about 0.55 ng/ml/mg to about 1.5 ng/ml/mg and most preferably about 0.60 ng/ml/mg to about 1.25 ng/ml/mg, and a dose adjusted area under the plasma concentration ($AUC_{0-\infty/dose}$) of about 100 ng·hr/ml/mg to about 300 ng·hr/ml/mg, preferably about 125 ng·hr/ml/mg to about 275 ng·hr/ml/mg and most preferably about 150 ng·hr/ml/mg to about 250 ng·hr/ml/mg.

A further embodiment of the present invention is a liquid composition comprising the fingolimod or pharmaceutically acceptable salt, conjugate or complex thereof, and pharmaceutically acceptable excipients such as a MFC, a sugar alcohol, preferably an NCF sugar alcohol, a solubilizing agent or combinations thereof. The liquid composition is filled into individual molds and the liquid removed by freeze drying to create a solid dosage form for oral administration or freeze dried particles that may be incorporated into a solid dosage form for oral administration.

A still further embodiment of the present invention is a liquid composition comprising the fingolimod or pharmaceutically acceptable salt, conjugate or complex thereof, and pharmaceutically acceptable excipients such as the MFC, a sugar alcohol, preferably an NCF sugar alcohol, a solubilizing agent or combinations thereof. The liquid composition is filled into individual molds and the liquid removed by vacuum drying to create a solid dosage form for oral administration or vacuum dried particles that may be incorporated into a solid dosage form for oral administration.

Another embodiment of the present invention is a fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or a mixture thereof and solid dosage forms containing the fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or mixture thereof.

DETAILED DESCRIPTION OF THE INVENTION

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "rapidly disintegrates in a patient's oral cavity" is intended to refer to a solid dosage form comprising a therapeutically effective amount of fingolimod or pharmaceutically acceptable salt, conjugate or complex thereof that dissolves or disintegrates in a test subject's oral cavity in less than 2.5 minutes, preferably less than 2.0 minutes and most preferably less than 1.5 minutes. In certain embodiments the solid dosage form should dissolve or disintegrate between about 5 seconds and about 60 seconds, preferably between about 7 seconds and about 45 seconds, and most preferably between about 10 seconds to about 30 seconds when placed in a patient's oral cavity such as on or under the tongue or between the test subject's cheek and gum. When measuring the amount of time needed for the solid dosage form to completely disintegrate or dissolve in a test subject's mouth, the solid dosage form is placed on the test subject's tongue; a chronometer, such as a stop watch, is started as soon as the solid dosage form contacts the tongue. The test subject is instructed that the tablet may be gently moved around the oral cavity without biting, chewing, or sucking on the solid dosage from. The test subject is instructed to immediately stop the chronometer after the last noticeable particle is disintegrated. This test is repeated with the same subject at least three times and the times are averaged.

As used herein, the term "rapidly disintegrates" is intended to refer a solid dosage form comprising a therapeutically effective amount of fingolimod or pharmaceutically acceptable salt, conjugate or complex thereof that disintegrates when tested in accordance with the USP procedure and apparatus described in <701> Disintegration. The time to disintegrate should be 2.5 minutes or less, preferably 2.0 minutes or less, and more preferably 1.5 minutes or less.

As used herein, the term "friability" refers to a physical strength measurement of a solid dosage form such as a tablet, and is defined as the ability of the solid dosage form to resist abrasion and attrition. It is typically measured by turning tablets in a rotating vessel and determining weight loss. These rotating devices are called "friabilators." The friabilator provides frictional abrasion to the sample and is used to measure the resistance to abrasion or attrition of samples. The loss of weight is measured after a fixed number of revolutions of a drum rotating at a controlled rate.

A friabilator apparatus typically uses a 285 mm drum of transparent synthetic polymer with polished internal surfaces. One side of the drum is removable. The samples are tumbled at each turn of the drum by a curved projection that extends from the middle of the drum to the outer wall. The drum is attached to the horizontal axis of a device that rotates at about 25 rpm to about 30 rpm. Thus, at each turn, the samples roll or slide and fall onto the drum wall or onto each other. Many such apparatuses are commonly available, e.g., the Roche type friabilator (Van Kel Industries, Inc., Edison, N.J.); a Erweka Friability Apparatus (Erweka Instruments, Milford, Conn.) (Bi (1996) supra, Chowhan (1982) J. of Pharm. Sci. 71:1371-1375), and the like.

In one exemplary protocol, the standard USP protocol described in section <1216> for measuring friability is used. Briefly, the predetermined number of samples are placed in a friabilator that is a 285 mm drum, about 39 mm in depth, of transparent synthetic polymer. The samples are "tumbled" at each turn of the drum by a curved projection that extends from the middle of the drum. The drum is rotated for about four minutes at about 25 rpm, resulting in a total of 100 rotations. A minimum of about 20 samples are used in any test, unless the samples weigh over 650 mg, in which case only 10 samples are used. After the allotted time, the samples are removed from the friabilator, and, with the aid of air pressure or a brush, adhering particles and dust are removed, and the remaining samples are accurately weighed and the percent loss of weight is calculated.

As used herein, the term "hardness" refers to the physical strength measurement of the solid dosage form such as a tablet. The resistance of a solid dosage form to chipping, abrasion, or breakage under conditions of storage, transportation, and handling before usage depends on its hardness, or "crushing strength." The "crushing" or "tensile" strength of a solid dosage form is defined as the force required to break a solid dosage form by compression in the radial direction. It is typically measured using one of the many commonly available tablet hardness testers. For example, "Stokes" and "Monsanto" hardness testers measure the force required to break the tablet when the force generated by a coil spring is applied diametrically to the tablet. A "Strong-Cobb" hardness tester also measures the diametrically applied force required to break a tablet, the force applied by an air pump forcing a plunger against the tablet placed on an anvil. Electrically operated hardness testers, such as the Schleuniger apparatus (also known as a "Heberlein") can be used.

As used herein, the term "normal storage conditions" refers to storage at room temperature, approximately 25° C. and approximately 60% relative humidity for at least three months, preferably at least six months, and most preferably at least one year. The solid dosage form in accordance with the present invention should be stored in pharmaceutically acceptable containers such as glass bottles, plastic bottles, metal foil pouch, or blister packaging with or without a desiccant.

As used herein, the term "accelerated storage conditions" refers to storage at approximately 40° C. and approximately 75% relative humidity for at least two weeks or longer, one month or longer, two months or longer, three months or longer, four months or longer, five months or longer, or six months or longer. The solid dosage form in accordance with the present invention should be stored in pharmaceutically acceptable containers such as glass bottles, plastic bottles, metal foil pouch, or blister packaging with or without a desiccant.

As used herein, the term "amorphous" indicates that the material, more particularly, a sugar alcohol in the solid dosage form lacks a defined crystal lattice structure. Whether the material is in an amorphous state can be determined by any of the known analytical techniques. One way used to determine if the sugar alcohol is in an amorphous state is to conduct an x-ray powder diffraction test.

As used herein, the term "substantially" as used to describe, for example, the amount of amorphous sugar alcohol present in a dried matrix of the fingolimod and CAF sugar alcohol means at least 5% or greater, 10% or greater, 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, or 95% or greater of the CAF sugar alcohol is present in an amorphous form.

As used herein moisture facilitating compounds ("MFC") refers to pharmaceutical excipients that are hygroscopic as well as CAF sugar alcohols. More specifically, MFCs include CAF sugar alcohols as described in detail below and pharmaceutically acceptable excipients, preferably solid water soluble excipients, that absorb at least 10 wt %, preferably 15 wt % and most preferably 20 wt % of water based on the total dry weight of the excipient when the excipient is placed in an open container and stored at 25° C. and 75% relative humidity, preferably at 25° C. and 85% relative humidity, until a constant weight gain is obtained, i.e., until equilibrium is obtained, or for at least 24 hours, preferably at least for 12 hours and most preferably at least 6 hours. Examples of MFC materials include but are not limited to citric acid, povidone, hydroxyethyl cellulose, and hydroxypropyl cellulose.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, unless indicated otherwise, references to fingolimod include fingolimod in its free base form, or as a pharmaceutically acceptable salt, conjugate, complex, solvate or hydrate of the free base or salt forms, or derivatives thereof. Preferably, fingolimod is in the form of a pharmaceutically acceptable acid addition salt, and more preferably, fingolimod is in the form of its hydrochloride salt. Alternatively, the fingolimod is a salt, conjugate or complex formed by reacting fingolimod, preferably a fingolimod anionic salt such as fingolimod HCl with an anionic $C_{10}$-$C_{30}$ carboxylic acid, an anionic $C_{10}$-$C_{30}$ alcohol, an anionic sulfate, an anionic sulfite or mixture thereof.

In certain embodiments of the present invention the fingolimod is fingolimod HCl in crystalline form, preferably one of the crystalline forms described in U.S. Pat. No. 8,530,522 which is incorporated herein by reference. One particular crystalline form is a hydrate crystal having a water content from about 5.2 to about 10.6 and exhibiting an X-ray powder diffraction pattern with peaks at about 2.9, about 8.6, about 17.2, about 24.4, about 25.9, about 28.2 and about 30.6. In alternative embodiments, particularly the embodiments prepared by dry blending, the fingolimod HCl may be the previously described hydrate crystal or it may be fingolimod HCl Form I described in U.S. Pat. No. 8,530,522 which exhibits an X-ray powder diffraction pattern with peaks at about 3.55, about 7.12, about 10.71, about 12.48, about 15.42 and about 20.59; fingolimod HCl Form II described in U.S. Pat. No. 8,530,522 which exhibits an X-ray powder diffraction pattern with peaks at about 3.47, about 6.92, about 10.38, about 14.58, about 19.20, about 20.34 and about 20.86; fingolimod HCl Form III described in U.S. Pat. No. 8,530,522 which exhibits an X-ray powder diffraction pattern with peaks at about 3.46, about 6.88, about 10.32, about 14.41, about 18.94, about 20.26, about 20.73 and about 24.23 or mixtures thereof. The fingolimod HCl in the final dosage forms of the present invention may comprise one or more of the afore-described crystal forms or it may also comprise an amorphous form. The particular form, i.e., crystal, amorphous or mixture thereof, of the fingolimod HCl in the final dosage form will depend upon the manufacturing method employed to prepare the dosage form and the storage conditions.

The fingolimod HCl employed in the preparation of the dosage forms of the present invention can have a range of particle sizes. In certain embodiments the fingolimod should be micronized and exhibit a mean particle size (d50) of less than 50 microns, preferably less than 35 microns and most preferably less than 20 microns. The mean particle size may be determined by any method commonly employed in the pharmaceutical arts, some of which are described in *Remington, The Science and Practice of Pharmacy* 21$^{st}$ ed. (2005) pp. 706-711 which is incorporated herein by reference.

Alternatively, in certain embodiments of the present invention the fingolimod comprises a fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or mixture thereof. In certain further embodiments of the present invention, the fingolimod comprises a mixture of fingolimod HCl and a fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or mixture thereof.

As used herein, and unless otherwise defined, the phrase "pharmaceutically acceptable salt" refers to any salt of fingolimod which retains the biological effectiveness of fingolimod. Examples of pharmaceutically acceptable salts include, but are not limited to, acetates, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phenylbutyrates, citrates, lactates, gamma-hydroxybutyrates, glycollates, tartarates, alkanesulfonates (e.g. methane-sulfonate or mesylate), propanesulfonates, naphthalene-1-sulfonates, naphthalene-2-sulfonates, and mandelates. Several of the officially approved salts are listed in *Remington, The Science and Practice of Pharmacy* 21$^{st}$ ed. (2005).

The pharmaceutically acceptable solid dosage forms of the present invention should comprise a therapeutically effective amount of fingolimod or a pharmaceutically acceptable salt, conjugate or complex thereof. The therapeutically effective amount can be easily determined from a review of the available literature and can range from about 0.1 mg to about 50 mg, preferably about 0.15 mg to about 25 mg, and most preferably about 0.2 mg to about 5 mg.

In addition to the fingolimod and pharmaceutically acceptable salts, conjugates and complexes thereof, the solid dosage forms of the present invention may comprise one or more sugar alcohols. If more than one sugar alcohol is employed, it is preferred that one of the sugar alcohols is a sugar alcohol that easily converts from a crystalline form to an amorphous form, i.e., a CAF sugar alcohol, and the other sugar alcohol is a sugar alcohol that does not easily convert from a crystalline form to an amorphous form, i.e., a NCF sugar alcohol. Examples of sugar alcohols that may be used in the present invention include arabitol, mannitol, sorbitol, dextrose, dextrin, sucrose, maltose, xylitol, maltitol, lactitol, erythritol, isomalt and mixtures thereof. It is believed that sugar alcohols that may easily convert from a crystalline form to an amorphous form, i.e., CAF sugar alcohols, exhibit a glass transition temperature of about 15° C. or higher after being dried to a constant weight, preferably a glass transition temperature of about 20° C. or higher after being dried to a constant weight, and most preferably a glass transition temperature of about 25° C. or higher after being dried to a constant weight. Examples of sugar alcohols that may easily convert from a crystalline form to an amorphous form include maltitol, lactitol, erythritol, and isomalt. Lactitol is a preferred CAF sugar alcohol.

It is also believed that sugar alcohols that do not easily convert from a crystalline form to an amorphous form, i.e., NCF sugar alcohols exhibit a glass transition temperature of about 10° C. or lower after being dried to a constant weight, preferably a glass transition temperature of about 5° C. or lower after being dried to a constant weight, and most preferably a glass transition temperature of about 0° C. or lower after being dried to a constant weight. Examples of sugar alcohols that do not easily convert from a crystalline form to an amorphous form, i.e., NCF sugar alcohols include mannitol, sorbitol, xylitol, sucrose, and maltose. Mannitol, xylitol, and sucrose are preferred NCF sugar alcohols.

In certain embodiments of the present invention, the solid dosage forms comprise the fingolimod and pharmaceutically acceptable salts, conjugates and complexes thereof, one or more NCF sugar alcohols as previously described and a MFC excipient.

The solid dosage forms of the present invention may comprise about 10 wt % to about 99 wt % of one or more sugar alcohols, preferably about 15 wt % to about 97 wt %, and most preferably about 20 wt % to about 95 wt %. In embodiments wherein a mixture of one or more MFC excipients, such as CAF sugar alcohol, and an NCF sugar alcohol are used, the amount of MFC, preferably CAF sugar alcohol, may comprise about 0.5 wt % to about 70 wt % of the total weight of the solid dosage form, preferably about 1 wt % to about 50 wt % of the total weight of the solid dosage form, and most preferably about 5 wt % to about 25 wt % of the total weight of the solid dosage form.

In certain embodiments of the present invention wherein a mixture of CAF and NCF sugar alcohols are employed, the ratio of CAF sugar alcohols to NCF sugar alcohols present in the solid dosage forms of the invention range from about 1(CAF):1(NCF) to about 1(CAF):20(NCF), preferably about 1(CAF):1(NCF) to about 1(CAF):15(NCF), and most preferably about 1(CAF):1(NCF) to about 1(CAF):10 (NCF).

The pharmaceutically acceptable solid dosage form of the present invention may further comprise conventional pharmaceutically acceptable excipients such as lubricants, fillers, binders, disintegrants, glidants, solubilizing agents, flavoring agents, gas producing agents, pH adjusting agents, antioxidants or mixtures of the foregoing. The amount of these excipients present in the solid dosage forms will vary depending upon the specific and desired properties of the solid dosage form. Ranges and amounts of these excipients are known and reported in the literature.

Examples of lubricants that may be employed in the solid dosage form of the present invention include magnesium stearate, sodium stearyl fumarate, stearic acid, glyceryl behenate, polyethylene glycols (preferably wherein the polyethylene glycol has a molecular weight of 6000 or more), polyoxyethylene stearate, magnesium lauryl sulfate, sodium oleate, and mixtures thereof. The lubricants may be present in an amount ranging from about 0.1 wt % to about 10 wt % based on the total weight of the dosage form, preferably about 0.2 wt % to about 7 wt %, and most preferably about 0.5 wt % to about 5 wt %.

Examples of fillers that may be employed in the solid dosage form of the present invention include dibasic calcium phosphate, microcrystalline cellulose, calcium carbonate, magnesium carbonate, calcium sulfate, powdered cellulose, silicified microcrystalline cellulose, magnesium carbonate, magnesium oxide, starch, and mixtures thereof.

Examples of binders that may be employed in the solid dosage form of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. If the binder is a polymeric binder, it is preferred that the binder have a low molecular weight and/or exhibit a viscosity of less than 200 mPa s, preferably less than 100 mPa s, and most preferably less than 50 mPa s when tested at a concentration of 2% (w/v) aqueous preparation at 20° C.

Binders impart cohesiveness to the solid dosage form and ensure strength of the solid dosage form, especially a tablet after compression. The use of water soluble binders are also important in the embodiments of the present invention that include a humidification step, because it is believed that the water soluble binder will swell upon absorption of the water, allowing more thorough hydration of the other components of the formulation and deeper penetration of the water into the solid dosage form. These water soluble binders may also functions as an MFC. A non-saccharide, water soluble polymeric binder may also act as a disintegrant, contributing to the rapid disintegration properties of the solid dosage form. The non-saccharide, water soluble polymeric binder also contributes to and enhances the "smooth feeling" of the solid dosage form when it dissolves in the patient's oral cavity.

Povidone is an example of a preferred non-saccharide, water-soluble, polymeric binder that may be used in the present invention. Povidone can be obtained from a variety of commercial sources, under tradenames such as KOLLIDON® or PLASDONE®. Povidone is commercially available in a variety of "K-values" which describe the approximate molecular weights. Although any of the commercially available K grades can be used in the present invention, those with a K value of 30 or less are preferred. In alternative embodiments, the non-saccharide, water soluble, polymeric binder can be derivatives of povidone such as a copolymer of N-vinyl pyrrolidone and vinyl acetate (also known as copovidone), 3-methyl N-vinylpyrrolidone, N-vinyl amide pyrrolidone, and the like or mixtures thereof.

Another preferred binder that may be used in the present invention is a low substituted hydroxypropyl cellulose which exhibits a low viscosity when dissolved in water and has no less than 5% and no more than 16% hydroxypropoxy groups. A more detailed description of some of the low substituted hydroxypropyl celluloses can be found in U.S. Pat. No. 7,399,485 which is incorporated herein by reference.

Still another preferred binder that may be used in the present invention is gelatin, such as that described in U.S. Pat. Nos. 4,305,502 and 4,371,516 which are incorporated herein by reference.

Examples of disintegrants that may be employed in the solid dosage form of the present invention include croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminum silicate, methylcellulose, sodium alginate, and mixtures thereof.

Examples of glidants that may be employed in the solid dosage form of the present invention include colloidal silicon dioxide, corn starch, talc and mixtures thereof.

One or more solubilizing agents may be employed in the dosage forms of the present invention. The solubilizing agent will aid in dissolving the fingolimod following administration of the dosage form to the patient. Examples of solubilizing agents that may be used in various embodiments of the present invention include but are not limited to cyclodextrins, surfactants (sometimes referred to as wetting agents) and mixtures thereof.

Cyclodextrins are cyclic oligosaccharides, consisting of alpha-1,4-linked alpha-D-glucopyranose units, with a lipophilic central cavity and hydrophilic outer surface. In aqueous solutions, cyclodextrins form inclusion complexes with drugs such as fingolimod, through a process in which the water molecules located in the central cavity are replaced by all or part of the drug molecule. The cyclodextrin may be an alpha, beta, or gamma type cyclodextrin, alpha, beta, or gamma type cyclodextrin derivatives or a combination thereof. The cyclodextrin derivatives include but are not limited to alkylated cyclodextrins, hydroxyalkyl cyclodextrins, sulfoalkylether cyclodextrins and branched cyclodextrins such a glucosyl- and maltosyl-cyclodextrins. Examples of the alkylated cyclodextrins include methyl-, ethyl-, propyl-, butyl-, and pentyl-cyclodextrins. Examples of hydroxyalkyl cyclodextrins include hydroxylethyl-, hydroxypropyl-, hydroxylbutyl- and hydroxypentyl-cyclodextrin. Other possible cyclodextrins that may be used in the present invention can be found in WO 2008/015695 which is incorporated herein by reference. The cyclodextrin may be present in the dosage forms of the present invention in an amount from about 0.1 wt % to about 30 wt % based upon the total weight of the dosage form, preferably about 0.5 wt % to about 20 wt %, and most preferably about 1 wt % to about 15 wt %.

The surfactant employed in the present invention may be a non-ionic surfactant, an ionic surfactant or a combination thereof. Examples of non-ionic surfactants include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants can be found on pages 1243-1249 of Martindale, The Extra Pharmacopoeia 29$^{th}$ ed. which is incorporated herein by reference.

In certain embodiments, the non-ionic surfactants may comprise fatty alcohol acid or amide ethoxylates, monoglyceride ethoxylates, sorbitan ester ethoxylates alkyl polyglycosides, mixtures thereof, and the like. Certain non-ionic surfactants include polyoxyethylene derivatives of polyol esters, such as Polysorbate 20 (TWEEN 20®), Polysorbate 40 (TWEEN 40®) Polysorbate 60 (TWEEN 60®), and Polysorbate 80 (TWEEN 80®).

In certain embodiments, the non-ionic surfactant may also comprise d-alpha tocopheryl polyethylene glycol 1000 succinate (TPGS), nonoxinols, poloxamers, sorbitan monolaurate, sorbitan monooleate, sorbitan monopalmitate, sorbitan monostearate, sorbitan sesquioleate, sorbitan trioleate, tyloxapol, and mixtures of the foregoing.

Any of a variety of ionic surfactants may also be incorporated into the solid dosage forms of the present invention compositions. Suitable ionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, phosphates, quaternary ammonium salts, and ethoxylated amines. Certain embodiments of the present invention will employ an anionic surfactant such as aluminum monostearate, calcium stearate, sulfated castor oil, sodium cetostearyl sulfate, sodium lauryl sulfate, sodium oleate, potassium oleate, zinc oleate, sodium stearate, sodium tetradecyl sulfate and mixtures therefore. The more preferred anionic surfactants are water soluble and may for a complex or derivative of fingolimod when dissolved in an aqueous solution containing a dissolved fingolimod salt. An example of a preferred anionic surfactant is sodium lauryl sulfate.

The surfactant may be present in the dosage forms of the present invention in an amount from about 0.01 wt % to about 10 wt % based upon the total weight of the dosage form, preferably from about 0.1 wt % to about 7 wt %, and most preferably from about 0.5 wt % to about 5 wt %. If an anionic surfactant is employed, the molar ratio of anionic surfactant to fingolimod should range from about 0.5 moles of anionic surfactant to about 3 moles of anionic surfactant for each mole of fingolimod present in the dosage form, preferably about 0.75 moles of anionic surfactant to about 2 moles of anionic surfactant for each mole of fingolimod present in the dosage form and most preferably about 0.85 moles of anionic surfactant to about 1.5 moles of anionic surfactant for each mole of fingolimod present in the dosage form.

Examples of flavoring agents that may be employed in the solid dosage form of the present invention include artificial sweeteners such as aspartame, saccharin, dipotassium glycyrrhizinate, stevia, thaumatin, and flavorants such as citric acid, peppermint oil, wintergreen oil, menthol, lemon, lime, orange, grape, cherry, and vanilla extract. Additional taste enhancing agents are described in U.S. Pat. No. 6,027,746 which is incorporated herein by reference.

Examples of gas producing agents, sometimes referred to as effervescent agents, that may be employed in the solid dosage form of the present invention include any compound that evolves gas by means of a chemical reaction when exposed to water or saliva. The gas producing agent typically comprises an acid source and a source of carbon dioxide. The acid source can be any of the pharmaceutically acceptable acids discussed below. The carbon dioxide source includes, but is not limited to, carbonate and bicarbonate salts, such as sodium bicarbonate, sodium carbonate, potassium bicarbonate, potassium carbonate, magnesium carbonate and mixtures thereof.

Examples of pH adjusting agents that may be employed in the solid dosage forms of the present invention include pharmaceutically acceptable acids or bases which may be present to adjust the pH of intermediate compositions leading up to the final solid dosage form and to adjust the pH of the drug environment of final solid dosage form to a desired or optimum pH range. Representative examples of pharmaceutically acceptable acids that may be used include, but are not limited to, acetic acid, citric acid, fumaric acid, hydrochloric acid, malic acid, nitric acid, phosphoric acid, propionic acid, sulfuric acid, tartaric acid, and mixtures thereof. Representative examples of pharmaceutically acceptable bases that may be used include but are not limited to ammonia, ammonium carbonate, diethanolamine, potassium hydroxide, sodium bicarbonate, sodium carbonate, sodium hydroxide, trolamine, and mixtures thereof.

Examples of antioxidants that may be employed in the solid dosage forms of the present invention include ascorbic acid, ascorbyl palmitate, butylated hydroxyanisole, butylated hydroxytoluene, hypophosphorous acid, monothioglycerol, potassium metabisulfate, propyl gallate, sodium bisulfite, sodium formaldehyde sulfoxylate, sodium metabisulfate, sodium sulfate, sodium thiosulfate, sodium dioxide, tocopherol, and mixtures thereof. The antioxidant may be present in the dosage forms of the present invention in an amount from about 0.01 wt % to about 20 wt % based upon the total weight of the dosage form, preferably from about 0.1 wt % to about 10 wt %, and most preferably from about 0.5 wt % to about 5 wt %.

The term "chelating agent," as used herein, means a molecule containing two or more electron donor atoms that can form coordinate bonds to a single metal ion. The term "chelating agent" is understood to include the chelating agent as well as pharmaceutically acceptable salts thereof. For example, the term "chelating agent" includes citric acid as well as its salt forms. Examples of chelating agents that may be used in the present invention include polyphosphates (e.g., sodium tripolyphosphate, hexametaphosphoric acid, sodium acid pyrophosphate, sodium pyrophosphate, tetra sodium pyrophosphate, sodium hexametaphosphate, sodium metaphosphate); aminocarboxylic acids (e.g., ethylenediaminetetraacetic acid (EDTA), 1,2-bis(2-amino-phenoxy) ethane-N,N,N'N'-tetraacetic acid (EGTA), ethylenebis(oxyethylenenitrilo)tetraacetic acid (BAPTA), N-(hydroxyethyl)-ethylenediaminetriacetic acid (HEDTA), diethylenetriaminepentaacetic acid (DTPA), N-dihydroxyethylglycine (2-HxG), ethylenebis(hydroxyphenyl-glycine) (EHPG), glutamic acid, aspartic acid, glycine, lysine); 1,3-diketones (e.g., acetylacetone, trifluoroacetylacetone, thenoyltrifluoroacetone, ascorbic acid); hydroxycarboxylic acids (e.g., tartaric acid, citric acid, malic acid, gluconic acid, ferulic acid, lactic acid, glucuronic acid); polyamines (e.g., dietheylenetriamine, triethylenetriamine); aminoalcohols (e.g., triethanolamine, N-hydroxyethyl ethyl ene-diamine, aminoethylethanolamine (AEEA); phenols (e.g., disulfopyrocatechol, chromotropic acid); aminophenols (e.g., oxinesulfonic acid); Schiff bases (e.g., disalicylaldehyde 1,2-propylenediimine); tetrapyrroles (e.g., tetraphenylporphin, phthalocyanine); silicates (aluminum calcium silicate, calcium silicate, sodium aluminosilicate sodium calcium aluminosilicate (hydrates), tricalcium silicate); sulfur compounds (e.g., potassium ethyl xanate, sodium diethyldithiocarbamate, diethyl dithiophosphoric acid, thiourea, magnesium sulfate); synthetic macrocyclic compounds (e.g., hexamethyl-[14]-4,11-dieneN.sub.4, 2,2,2-cryptate); polymers (e.g., polyethyleneimines, polymethacryloylacetone, poly(p-vinylbenzyliminodiacetic acid)), phosphonic acids (e.g., nitrilotrimethylenephosphonic acid, ethylenediaminetetra-(methylenephosphonic acid), hydroxyethylidenediphosphonic acid) or combinations thereof.

The amount of chelating agent present in the oral dosage form of the present invention will depend on the particular chelating agent or agents (i.e. mixtures of chelating agents) selected. Generally, the amount will range from about 0.5 wt % to about 15 wt % based upon the total weight of the dosage form, preferably from about 0.75 wt % to about 10 wt %, and most preferably from about 1 wt % to about 5 wt %.

The solid dosage form of the present invention may be prepared by any method commonly known in the pharmaceutical arts such as wet granulation, slugging and/or dry mixing the fingolimod with the selected excipients and forming the granules, aggregates or mixtures into tablets. Because the oral doses of fingolimod are 5 mg or less, typically in the range of about 0.25 mg to about 1.0 mg, preparing a solid dosage form such as a tablet with a uniform and consistent distribution of fingolimod, i.e., content uniformity, can be difficult. The dosage forms of the present invention exhibit a consistent distribution of fingolimod throughout the dosage form and more importantly, exhibit a consistent distribution of fingolimod throughout the composition blend that is used to fill the tablet dies prior to pressing the composition blend into the tablets. This consistent distribution in the composition blend means that samples taken from the same composition blend will not deviate by more than 5%, preferably will not deviate by more than 3%, and most preferably will not deviate by more than 2% in the amount of fingolimod. Moreover, if the dosage form of the present invention is a tablet, the content of the fingolimod in the tablet should be about 90% to about 110% of the theoretical amount of the tablet and subsections or divisible portions of the tablet should also contain about 90% to about 110%, preferably about 93% to about 107%, and most preferably about 95% to about 105% of the theoretical amount of the subsection of tablet. By way of example, if a tablet prepared in accordance with the present invention contains a target or theoretical amount of 1 mg of fingolimod, acceptable samples of the tablet may contain about 0.9 mg to about 1.1 mg. If the 1 mg tablet is divided in half, each half should contain a target or theoretical amount of 0.5 mg of fingolimod, acceptable samples of the halved tablet may contain about 0.45 mg to about 0.55 mg of fingolimod.

If the dosage form of the present invention is a tablet, it may comprise a score, indentation or demassed region that will allow the tablet to be divided into subsections or portions, thereby allowing the patient to administer divided or subdoses. For example if the tablet of the present invention contains a target or theoretical amount of 1 mg of fingolimod, the tablet may be divided into two approximately equal halves to allow the patient to administer a single 0.5 mg dose as may be instructed by a physician.

Similarly, a 0.5 mg tablet could be divided into two 0.25 mg halves. The accurate division is enabled by breaking the tablet along a predetermined scored, indented or demassed region of the tablet. The predetermined scored, indented or demassed region may be on one or more surfaces of the tablet. For example, the predetermined score, indentation or demassed region may be on the top, bottom, sides, top and bottom, or top, bottom and sides of the tablet. The score, indentation or demassed region may be formed into the tablet during the compression step by employing a die shape that creates the score, indentation or demassed region. The score, indentation or demassed region may also be formed after the tablet has been formed such as by the use of a laser to remove a portion of the tablet material.

In certain embodiments of the present invention, the solid dosage form of the present invention can be prepared by dissolving or suspending the fingolimod or a pharmaceutically acceptable salt thereof, such as the HCl salt, in a suitable solvent such as water, an organic solvent such as $C_1$-$C_6$ branched or straight chain alcohols, ethers, esters or ketones or mixtures thereof along with additional pharmaceutical excipients such as binders, solubilizing agents, antioxidants, chelating agents and mixtures thereof and spraying the resulting fingolimod solution onto a substrate comprising at least one pharmaceutical acceptable excipient such as a sugar alcohol, filler or mixture thereof to create fingolimod granules. The fingolimod granules may be dried, and sized if necessary. The dried and sized fingolimod granules can be blended with additional pharmaceutical excipients such as a lubricant and compressed into a tablet.

In certain embodiments, the solid dosage form of the present invention is prepared by dissolving the fingolimod or a pharmaceutically acceptable salt thereof, such as the HCl salt, in a suitable solvent such as water, an organic solvent such as $C_1$-$C_6$ branched or straight chain alcohols, ethers, esters or ketones or mixtures thereof along with at least one solubilizing agent and additional pharmaceutical excipients such as MFCs, fillers (including sugar alcohols), binders, antioxidants, chelating agents and mixtures thereof and spraying the resulting fingolimod solution onto a substrate comprising at least one pharmaceutical acceptable excipient such as an MFC, a sugar alcohol, filler or mixture thereof to create fingolimod granules. The fingolimod granules may be dried, and sized if necessary. The dried and sized fingolimod granules can be blended with additional pharmaceutical excipients such as a lubricant and compressed into a tablet. In certain embodiments, the solubilizing agent employed in this method is a cyclodextrin and should be used in an amount to fully complex the fingolimod. Preferably the weight ratio of fingolimod to cyclodextrin should be at least about 1:5 to about 1:40 or higher, preferably at least about 1:7.5 to about 1:30, most preferably at least about 1:10 to about 1:20. In other embodiments, the solubilizing agent employed in this method is a surfactant, preferably an ionic surfactant, and most preferably an anionic surfactant. If an ionic surfactant is employed it is should be present in a weight ratio of fingolimod to ionic surfactant of at least about 1:0.5 to about 1:10 or higher, preferably of at least about 1:0.75 to about 1:8 and most preferably at least about 1:1 to about 1:5. The anionic solubilizing agent employed in this embodiment may form a salt, conjugate, complex or co-precipitate with the fingolimod during the manufacturing process, i.e., during preparation of the granulating liquid or during the spray drying step. In certain embodiments employing an anionic surfactant such as sodium lauryl sulfate, molar ratio of anionic surfactant to fingolimod should range from about 0.5 moles of anionic surfactant to about 3 moles of anionic surfactant for each mole of fingolimod present in the dosage form, preferably about 0.75 moles of anionic surfactant to about 2 moles of anionic surfactant for each mole of fingolimod present in the dosage form and most preferably about 0.85 moles of anionic surfactant to about 1.5 moles of anionic surfactant for each mole of fingolimod present in the dosage form.

In certain embodiments of the present invention, the solid dosage form of the present invention can be prepared by dry mixing the fingolimod with at least one pharmaceutically acceptable excipient such as an MFC, a sugar alcohol, antioxidant, filler or mixtures thereof. The dry mixture is then granulated with a suitable solvent such as water, an organic solvent such as $C_1$-$C_6$ branched or straight chain alcohols, ethers, esters or ketones or mixtures. The granulating liquid comprising the suitable solvent may also comprise one or more pharmaceutical excipients such as binders, solubilizing agents, antioxidants, chelating agents and mixtures thereof. The fingolimod granules may be dried, and sized if necessary. The dried and sized fingolimod granules can be blended with additional pharmaceutical excipients such as a lubricant and compressed into a tablet.

In one embodiment, the solid dosage form of the present invention is prepared by first preparing a drug/MFC, preferably CAF sugar alcohol, liquid composition. The drug/MFC liquid composition comprises the fingolimod or pharmaceutically acceptable salt thereof, at least one MFC which is preferably at least one CAF sugar alcohol, a pharmaceutically acceptable solvent, optionally at least one solubilizing agent and optionally at least one antioxidant. The pharmaceutically acceptable solvent can be water, an organic solvent, or a combination thereof. The organic solvent can be any organic solvent commonly used in the manufacture of pharmaceutical products such as alcohols, ethers, and esters. Some of the preferred organic solvents are acetone and $C_1$ to $C_6$ alcohols such as methanol, ethanol, propanol, isopropanol, butanol, and combinations therefore.

The fingolimod or pharmaceutically acceptable salt thereof may be dissolved or suspended in the drug/MFC liquid composition. It is preferred that the fingolimod or pharmaceutically acceptable salt thereof is dissolved in the drug/MFC liquid composition and the MFC comprise at least one CAF sugar alcohol.

In the embodiments employing a CAF sugar alcohol, the CAF sugar alcohol should be dissolved in the drug/CAF sugar alcohol liquid composition. It is believed that dissolving the CAF sugar alcohol in the pharmaceutically acceptable solvent of the drug/CAF sugar alcohol liquid composition will allow the CAF sugar alcohol to be converted into an amorphous form and thereby be present in the solid dosage form of the present invention in part or substantially in an amorphous form.

In certain embodiments, an NCF sugar alcohol may also be dissolved or suspended in the drug/MFC liquid composition. Additional pharmaceutical excipients may also be dissolved or suspended in the drug/MFC liquid composition.

The drug/MFC liquid composition, with or without the NCF sugar alcohol and additional pharmaceutical excipients such as a solubilizing agent and an antioxidant, may be dried to create a drug/MFC matrix. The drying step can be accomplished by spray drying, freeze drying vacuum drying, oven drying, or a combination thereof.

If a spray drying step is employed, the drug/MFC liquid composition, with or without the NCF sugar alcohol and additional pharmaceutical excipients, is dried using known conventional spray drying apparatus such as those described in U.S. Pat. No. 5,587,180 and *Remington, The Science and Practice of Pharmacy*, $22^{nd}$ ed. (2013), pp. 791-792 which are incorporated herein by reference. The powder created by the spray drying of the drug/MFC liquid composition may be mixed with additional sugar alcohols such as NCF sugar alcohols and pharmaceutically acceptable excipients and further processed into a solid dosage form in accordance with the present invention. It is believed that the powder created by the spray drying step will contain a matrix comprising the fingolimod or pharmaceutically acceptable salt thereof and the MFC excipient. If the MFC excipient comprises at least one CAF sugar alcohol, the CAF sugar alcohol is present in the powder or matrix, either totally or substantially in part, in an amorphous form.

Alternatively, the drug/MFC liquid composition, with or without the NCF sugar alcohol and additional pharmaceutical excipients such as a solubilizing agent and an antioxidant, may be spray dried by using a conventional fluid bed granulator as described generally by *Remington, The Science and Practice of Pharmacy*, $22^{nd}$ ed. (2013), pp. 956-957 which is incorporated herein by reference. In this embodiment, the substrate in the fluidized bed onto which the drug/MFC liquid composition is sprayed may be a sugar alcohol, one of the pharmaceutically acceptable excipients previously described or a combination thereof. In a preferred embodiment, the substrate in the fluidized bed comprises all or part of the NCF sugar alcohol that is present in the solid dosage form. The coated substrate created by this spray drying of the drug/MFC liquid composition may be mixed with additional sugar alcohols such as NCF sugar alcohols and pharmaceutically acceptable excipients and further processed into a solid dosage form in accordance with the present invention. It is believed that the coating on the substrate will contain a matrix comprising the fingolimod or pharmaceutically acceptable salt thereof and the MFC excipient. If the MFC excipient comprises at least one CAF sugar alcohol, the CAF sugar alcohol may be present in the matrix, either totally or substantially in part, in an amorphous form. If a solubilizing agent is present in the liquid composition, the coating may also comprise, in whole in part, a salt, conjugate, complex or co-precipitate of the fingolimod and solubilizing agent.

In another embodiment, the fingolimod may be dissolved, suspended or disbursed in a suitable solvent along with additional pharmaceutical excipients such as a sugar alcohol, a solubilizing agent and an antioxidant and the resulting fingolimod solution, suspension or dispersion may be freeze dried using conventional freeze drying or lyophilization equipment and processes such as those described in U.S. Pat. Nos. 4,371,516 and 4,767,789, and *Remington, The Science and Practice of Pharmacy*, $22^{nd}$ ed. (2013), pp. 891-894 which are incorporated herein by reference. In this embodiment, the fingolimod solution, suspension or dispersion may be filled into preformed molds which are then lyophilized, creating the solid dosage forms of the present invention in situ, and the molds may be sealed and packaged for distribution. If the solid dosage form is to be prepared in situ by this method, it is preferred that at least one sugar alcohol, such as a CAF and/or NCF sugar alcohol and any additional pharmaceutically acceptable excipients such as a binder will included in the fingolimod solution, suspension or dispersion prior to freeze drying or lyophilization. It is also believed that if a CAF sugar alcohol is included in the fingolimod solution, suspension or dispersion, the resulting in situ formed solid dosage forms will contain a matrix comprising the fingolimod or pharmaceutically acceptable salt, conjugate or complex thereof and the CAF sugar alcohol wherein the CAF sugar alcohol is present, either totally or substantially in part, in an amorphous form. In a further embodiment, the freeze dried composition may be further processed by seizing and/or mixing the freeze dried composition with additional pharmaceutically acceptable excipients such as NCF sugar alcohols and lubricants and further processed into a solid dosage form in accordance with the present invention. Again, it is believed that the resulting mixture will contain the freeze dried particles that comprise a matrix comprising the fingolimod or pharmaceutically acceptable salt, conjugate, or complex thereof and the CAF sugar alcohol wherein the CAF sugar alcohol is present, either totally or substantially in part, in an amorphous form. It is also believed that the fingolimod and solubilizing agent if included in the liquid composition will be present in the solid matrix, in whole or in part, as a salt, conjugate or complex of the fingolimod and solubilizing agent.

In a further embodiment, the fingolimod may be dissolved, suspended or disbursed in a suitable solvent, with or without additional pharmaceutical excipients such as a CAF sugar alcohol, a NCF sugar alcohol, a solubilizing agent and an antioxidant, and the resulting fingolimod solution, suspension or dispersion may be vacuum dried using equipment and processes such as those described in U.S. Pat. No. 5,298,261 which is incorporated herein by reference. In this embodiment, as with the freezing method, the fingolimod solution, suspension or dispersion may be filled into preformed molds which are then vacuum dried, creating the solid dosage forms of the present invention in situ, and the molds may be sealed and packaged for distribution. If the solid dosage form is to be prepared in situ by this method, the sugar alcohol and any additional pharmaceutically acceptable excipients such as a binder should be present in the fingolimod solution, suspension or dispersion. It is believed that in situ formed solid dosage form prepared in the embodiment which also contain a CAF sugar alcohol in the fingolimod solution, suspension or dispersion will produce a matrix comprising the fingolimod or pharmaceutically acceptable salt thereof and the CAF sugar alcohol wherein the CAF sugar alcohol is present, either totally or substantially in part, in an amorphous form. In a further embodiment, the vacuum dried composition may be further processed by seizing and/or mixing the vacuum dried composition with additional pharmaceutically acceptable excipients such as NCF sugar alcohols and lubricants and further processed into a solid dosage form in accordance with the present invention. Again, it is believed that the resulting mixture will contain the vacuum dried particles that comprise a matrix comprising the fingolimod or pharmaceutically acceptable salt thereof and the CAF sugar alcohol wherein the CAF sugar alcohol is present, either totally or substantially in part, in an amorphous form. It is also believed that the fingolimod and solubilizing agent if included in the liquid composition may be present in the solid matrix, in whole or in part, as a salt, conjugate or complex of fingolmod and solubilizing agent.

In certain embodiments of the present invention, the fingolimod matrix resulting from the drying steps of the forgoing embodiments may be combined with additional pharmaceutically acceptable excipients and formed into a tablet, granule, or pellet for administration to a patient.

If a cyclodextrin is employed in the present invention, it should be incorporated into the fingolimod solutions, suspensions or dispersions described above prior to the application of the fingolimod solution, suspension or dispersion onto the substrate. The order in which the cyclodextrin and fingolimod are added to the solution, suspension or dispersion along with any additional desired excipients such as a MFC, binder or antioxidant are not critical, however the fingolimod solution, suspension or dispersion comprising the cyclodextrin should be stirred for a sufficient time to allow the fingolimod to complex with the cyclodextrin.

If an anionic surfactant is employed in the present invention, it should be incorporated into the fingolimod solutions, suspensions or dispersion described above prior to the application of the fingolimod solution, suspension or dispersion onto the substrate. The order in which the anionic surfactant and fingolimod are added to the solution, suspension or dispersion along with any additional desired excipients such as a MFC, binder or antioxidant are not critical, however the fingolimod solution, suspension or dispersion comprising the anionic surfactant should be stirred for a sufficient time to allow the fingolimod to react with the anionic surfactant if such as reaction is desired.

The solid dosage form of the present invention may also be prepared by dry blending the fingolimod with at least one sugar alcohol and at least one additional pharmaceutical excipient such as a lubricant and optionally an antioxidant and compressing the dry blend directly into a tablet. Alternatively, the fingolimod may be dry blended with at least one sugar alcohol and at least one additional pharmaceutical excipient and compressed using a roller compressor or tablet die. The resulting compressed material will be milled or ground to create fingolimod aggregates that may be further processed, such as blended with a lubricant, before being formed into the final dosage form, i.e., tablet, pellet or granule.

Once the final tablet, granule or pellet is prepared, it may subjected to a humidification step and a drying step such as described in U.S. Pat. No. 6,465,009 and which is incorporated herein by reference. More specifically, in order to provide for a tablet, granule, or pellet that is both rapidly disintegrating and has a relatively great strength (increased hardness), the method of this embodiment of the invention provides for a two-step treatment, which includes a humidification step and a drying step. Both treatments can be carried out in a single environmental chamber where both temperature and humidity can be accurately controlled. Many means to effect these steps are available and the invention is not limited by the use of any particular apparatus.

The treatment condition of the humidification step should be set at a lower temperature and a higher moisture level (higher relative humidity) than the drying step. The desired final product properties can be achieved by routine testing and optimization of treatment conditions that are dependent on individual formulations.

In the humidification step, water is absorbed into the tablet, granule or pellet. This absorption is enhanced when a water-soluble polymer binder, which may also function as an MFC, is present in the tablet, granule or pellet because the binder, as well as the tablet, granule or pellet, swells upon absorption of the water, allowing more thorough wetting (hydration) of the other components of the formulation and deeper penetration of the wetting agent (water) into the tablet interior. In the drying process, the water is removed from the tablet, granule or pellet. This loss of water in the drying process results in a harder tablet. Others have shown that a short humidification step (10 seconds to 30 minutes) followed by drying results in tablets with a relatively soft interior (as determined by the amount of force in the compression step) and a relatively harder outer (exterior) surface layer. The result is a tablet with a hardness sufficient to be further packaged, shipped and handled, yet still capable of rapidly disintegrating when placed in the oral cavity.

In different embodiments, the relative humidity (RH) in the humidification step is between about 50% and 100%, preferably between about 60% and about 85% and most preferably about 65% to about 80%; the humidification step lasts for between about 5 minutes to about 12 hours, preferably about 15 minutes to about 6 hours, and most preferably about 30 minutes to about 3 hours; and the temperature at which the humidification step is carried out can be between about 20° C. to about 50° C., preferably about 25° C. to about 45° C.

Different drying conditions can be used to achieve the desired dosage form hardness, which is measured after the dosage form is dried. This drying step is typically conducted in an oven at a temperature between 30° C. and 75° C. The temperature should be set below the melting point of the components in the tablet, granule, or pellet but higher than room temperature. The time for the drying can vary depending upon the dosage form and drying conditions. Generally, the dosage from should be dried until it has a moisture content of less than 5%, preferably less than 4%, and most preferably less than 3% as determined by standard pharmaceutical measurements such as Karl Fisher.

If the solid dosage form prepared in accordance with the present invention is a tablet, granule, or pellet, it should exhibit a hardness in the range of about 5 newtons (N) to about 350.0 N, preferably about 10 N to about 250 N, and most preferably about 15 N to about 150 N.

If the solid dosage form prepared in accordance with the present invention is a tablet, granule, or pellet, especially the solid dosage form that was subjected to humidification and drying, it should exhibit a friability of less than 2%, preferably less than 1.5%, and most preferably less than 1.0%.

Embodiments of the solid dosage forms of the present invention may dissolve in a patient's oral cavity in less than 2.5 minutes, preferably less than 2.0 minutes, and most preferably less than 1.5 minutes.

Embodiments of the solid dosage forms of the present invention may disintegrate when tested using a USP Disintegration apparatus and method in less than 2.5 minutes, preferably less than 2.0 minutes, and most preferably less than 1.5 minutes.

The solid dosage forms of the present invention should be stable. More specifically, the solid dosage forms of the present invention will contain about 2.0% or less of any individual fingolimod degradation product, preferably about 1.5% or less of any individual fingolimod degradation product, and most preferably about 1.0% or less of any individual fingolimod degradation product when the solid dosage form is stored in a sealed bottle, preferably a sealed plastic bottle such as a high density polyethylene bottle (with or without a desiccant) or a sealed aluminum foil pouch (with or without a desiccant), at approximately 25° C. and approximately 60% relative humidity for at least three months, preferably at least six months and most preferably at least one year and/or at approximately 40° C. and approximately 75% relative humidity for one month, two months, or three months.

The solid dosage forms of the present invention should also contain a total amount of fingolimod degradation products of about 2.5% or less, preferably about 2.0% or less, and most preferably about 1.5% or less when the solid dosage form is stored in a sealed bottle, preferably a sealed plastic bottle such as a high density polyethylene bottle (with or without a desiccant) or a sealed aluminum foil pouch (with or without a desiccant), stored at approximately 25° C. and approximately 60% relative humidity for at least three months, preferably at least six months, and most preferably at least one year and/or at approximately 40° C. and approximately 75% relative humidity for one month, two months, or three months.

The solid oral dosage forms of the present invention should exhibit a pharmacokinetic profile that is bioequivalent to the commercially available GILENYA® capsule product. As used herein "bioequivalent" is used in accordance with the United States Food and Drug Administration's ("FDA") definition. A more detailed description of the FDA's bioequivalence determination can be found in the FDA's Guidance for Industry Bioavailability and Bioequivalence Studies for Orally Administered Drug Products—General Considerations March 2003, and the FDA's Guidance for Industry Statistical Approaches to Establishing Bioequivalence January 2001 which are incorporated herein by reference. The FDA recommends in its August 2011 Draft Guidance on Fingolimod to conduct two pharmacokinetic studies to establish bioequivalence to the commercially available GILENYA® capsule product. The first study is a single-dose, two-way cross over study wherein three (3) 0.5 mg GILENYA® capsules for a total dose of 1.5 mg of fingolimod and a similar 1.5 mg dose of the test product are administered to healthy male and non-pregnant females under fasting conditions. The second study is similar to the first study except the dosing is conducted under fed (non-fasting) conditions. For purposes of the present invention the solid oral dosage forms of the present invention would be considered bioequivalent to the commercially available GILENYA® capsule product if the log transformed ratio of the $C_{max}$ and AUC for the solid oral dosage form of the present invention (test product) compared to the GILENYA® capsule(s) (reference product) are shown to be within 80-125%, using the 90% confidence interval. The log transformed ratio of the $C_{max}$ and AUC may be obtained from a single does or multiple dose randomized cross over study under fed, fasted or both fed and fasted conditions.

In certain embodiments of the present invention following a single dose administration of the dosage form of the present invention to healthy male and non-pregnant female subjects under fasted conditions, the subjects should exhibit a time to maximum fingolimod concentration ($T_{max}$) of about 8 to about 40 hours, preferably about 10 to about 35 hours and most preferably about 12 to about 30 hours, a dose adjusted maximum fingolimod concentration ($C_{max/dose}$) of about 0.50 ng/ml/mg to about 2.0 ng/ml/mg, preferably about 0.55 ng/ml/mg to about 1.50 ng/ml/mg, and most preferably about 0.60 ng/ml/mg to about 1.25 ng/ml/mg and a dose adjusted area under the plasma concentration ($AUC_{0-\infty/dose}$) of about 100 ng·hr/ml/mg to about 300 ng·hr/ml/mg, preferably about 125 ng·hr/ml/mg to about 275 ng·hr/ml/mg and most preferably about 150 ng·hr/ml/mg to about 250 ng·hr/ml/mg.

Another embodiment of the present invention is a fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or mixture thereof and solid dosage forms containing the fingolimod salt, conjugate or complex formed by reacting fingolimod with an anionic $C_{10}$-$C_{30}$ carboxylic acid, an anionic $C_{10}$-$C_{30}$ alcohol, an anionic sulfate, an anionic sulfite or mixture thereof. The fingolimod/anionic $C_{10}$-$C_{30}$ carboxylic acid, anionic $C_{10}$-$C_{30}$ alcohol, anionic sulfate, anionic sulfite salt, conjugate or complex may be formed by dissolving a fingolimod salt such as fingolimod HCl in a suitable solvent such as water, an organic solvent such as $C_1$-$C_6$ branched or straight chain alcohols, ethers, esters or ketones or mixtures thereof, adding an anionic $C_{10}$-$C_{30}$ carboxylic acid, an anionic $C_{10}$-$C_{30}$ alcohol, an anionic sulfate, an anionic sulfite or mixture thereof to the fingolimod solution and mixing the resulting reaction mass. Alternatively, the anionic $C_{10}$-$C_{30}$ carboxylic acid, anionic $C_{10}$-$C_{30}$ alcohol, anionic sulfate, anionic sulfite or mixture thereof may be dissolved in a suitable solvent, adding the fingolimod HCl added to the anionic $C_{10}$-$C_{30}$ carboxylic acid, anionic $C_{10}$-$C_{30}$ alcohol, anionic sulfate, anionic sulfite or mixture thereof solution and mixing the resulting reaction mass. The fingolimod/anionic $C_{10}$-$C_{30}$ carboxylic acid, anionic $C_{10}$-$C_{30}$ alcohol, anionic sulfate, anionic sulfite salt, conjugate or complex may also be formed by dissolving fingolimod HCl in a suitable solvent, dissolving the anionic $C_{10}$-$C_{30}$ carboxylic acid, anionic $C_{10}$-$C_{30}$ alcohol, anionic sulfate, anionic sulfite or mixture thereof in a suitable solvent, combing the fingolimod solution and the anionic $C_{10}$-$C_{30}$ carboxylic acid, anionic $C_{10}$-$C_{30}$ alcohol, an anionic sulfate, anionic sulfite or mixture thereof solution and mixing the resulting reaction mass. The solvent is removed from the resulting reaction mass by conventional techniques such as evaporation or filtration to isolate the fingolimod/anionic $C_{10}$-$C_{30}$ carboxylic acid, anionic $C_{10}$-$C_{30}$ alcohol, anionic sulfate, anionic sulfite or mixture thereof salt, conjugate or complex. The isolated fingolimod/anionic $C_{10}$-$C_{30}$ carboxylic acid, anionic $C_{10}$-$C_{30}$ alcohol, anionic sulfate, anionic sulfite or mixture thereof salt, conjugate or complex may be used in the solid dosage forms of the present invention. The isolated fingolimod/anionic $C_{10}$-$C_{30}$ carboxylic acid, anionic $C_{10}$-$C_{30}$ alcohol, anionic sulfate, anionic sulfite or mixture thereof salt, conjugate or complex may also be used in the solid dosage forms that do not contain a sugar alcohol.

The molar ratio of anionic $C_{10}$-$C_{30}$ carboxylic acid, anionic $C_{10}$-$C_{30}$ alcohol, anionic sulfate, anionic sulfite compound(s) to fingolimod in the reaction mass should range from about 0.5 moles of anionic $C_{10}$-$C_{30}$ carboxylic acid, anionic $C_{10}$-$C_{30}$ alcohol, anionic sulfate, anionic sulfite compound(s) to about 3 moles of anionic $C_{10}$-$C_{30}$ carboxylic acid, anionic $C_{10}$-$C_{30}$ alcohol, anionic sulfate, anionic sulfite compound(s) for each mole of fingolimod present in the reaction mass, preferably about 0.75 moles of anionic $C_{10}$-$C_{30}$ carboxylic acid, anionic $C_{10}$-$C_{30}$ alcohol, anionic sulfate, anionic sulfite compound(s) to about 2 moles of anionic $C_{10}$-$C_{30}$ carboxylic acid, anionic $C_{10}$-$C_{30}$ alcohol, anionic sulfate, anionic sulfite compound(s) for each mole of fingolimod present in the reaction mass and most preferably about 0.85 moles of anionic $C_{10}$-$C_{30}$ carboxylic acid, anionic $C_{10}$-$C_{30}$ alcohol, anionic sulfate, anionic sulfite compound(s) to about 1.5 moles of anionic $C_{10}$-$C_{30}$ carboxylic acid, anionic $C_{10}$-$C_{30}$ alcohol, anionic sulfate, anionic sulfite compound(s) for each mole of fingolimod present in the reaction mass. In a preferred embodiment, the anionic $C_{10}$-$C_{30}$ carboxylic acid, anionic $C_{10}$-$C_{30}$ alcohol, anionic sulfate, anionic sulfite or mixture thereof employed in the reaction mass is an anionic sulfate or anionic sulfite compound such as sodium metabisulfate or an anionic organosulfate or anionic oragansulfite compound such as an anionic $C_{10}$-$C_{30}$ carboxylic acid sulfate or an anionic $C_{10}$-$C_{30}$ alcohol sulfate or combinations thereof. Examples of anionic $C_{10}$-$C_{30}$ carboxylic acid, anionic $C_{10}$-$C_{30}$ alcohol, anionic sulfate, anionic sulfite compounds that may be used include but are not limited to sodium lauryl sulfate, sodium oleate, or sodium tetradecyl sulfate.

The fingolimod/anionic $C_{10}$-$C_{30}$ carboxylic acid, anionic $C_{10}$-$C_{30}$ alcohol, anionic sulfate, anionic sulfite salt, conjugate or complex may also be formed during or as part of the manufacturing of the solid dosage forms of the present invention.

In one embodiment of the present invention there is provided an orally disintegrating tablet comprising:
(a) 0.1 mg to 1.0 mg of fingolimod or a pharmaceutically acceptable salt, conjugate or complex thereof, and
(b) at least one sugar alcohol, and
wherein said tablet exhibits a friability of less than 2% and disintegrates when tested using a USP Disintegration apparatus in less than 2.5 minutes.

In one embodiment of the present invention there is provided a stable orally disintegrating tablet comprising:
(a) 0.1 mg to 1.0 mg of fingolimod or a pharmaceutically acceptable salt, conjugate, or complex thereof, and
(b) at least one sugar alcohol,
(c) a solubilizing agent, and
wherein said tablet exhibits a friability of less than 2% and disintegrates when tested using a USP Disintegration apparatus in less than 2.5 minutes, and wherein said tablet contains about 2.0% or less of any individual fingolimod degradation product and a total amount of fingolimod degradation products of about 2.5% or less when the solid pharmaceutical dosage form is stored in a sealed bottle or aluminum foil pouch at approximately 40° C. and approximately 75% relative humidity for one month.

In one embodiment of the present invention there is provided a stable orally disintegrating tablet which is bioequivalent to the 0.5 mg GILENYA® capsule comprising:
(a) 0.5 mg of fingolimod or a pharmaceutically acceptable salt, conjugate or complex thereof, and
(b) at least one sugar alcohol,
(c) a solubilizing agent, and
wherein said tablet exhibits a friability of less than 2% and disintegrates when tested using a USP Disintegration apparatus in less than 2.5 minutes, and
wherein said tablet contains about 2.0% or less of any individual fingolimod degradation product and a total amount of fingolimod degradation products of about 2.5% or less when the solid pharmaceutical dosage form is stored in a sealed bottle or aluminum foil pouch at approximately 40° C. and approximately 75% relative humidity for one month, and the log transformed $C_{max}$ and $AUC_{0-t}$ ratio of said tablet to said GILENYA® capsule is within 80-125%, using the 90% confidence interval.

In one embodiment of the present invention there is provided a stable orally disintegrating tablet which is bioequivalent to the 0.5 mg GILENYA® capsule comprising:
(a) 0.5 mg of fingolimod or a pharmaceutically acceptable salt, conjugate or complex thereof, and
(b) at least one sugar alcohol,
(c) a solubilizing agent, and
wherein said tablet exhibits a friability of less than 2% and disintegrates when tested using a USP Disintegration apparatus in less than 2.5 minutes, and
wherein said tablet contains about 2.0% or less of any individual fingolimod degradation product and a total amount of fingolimod degradation products of about 2.5% or less when the solid pharmaceutical dosage form is stored in a sealed bottle or aluminum foil pouch at approximately 40° C. and approximately 75% relative humidity for one month, and
wherein, following a single dose administration of the solid pharmaceutical dosage form under fasting conditions, the time to maximum fingolimod concentration ($T_{max}$) is about 8 to about 40 hours, the dose adjusted maximum fingolimod concentration ($C_{max/dose}$) is about 0.50 to about 2.0 ng/ml/mg and the dose adjusted area under the plasma concentration ($AUC_{0-\infty/dose}$) is about 100 to about 300 ng·hr/ml/mg.

As an especially preferred embodiment, the present invention provides an orally disintegrating tablet comprising:
(a) 0.1-1.0% by weight of fingolimod or a pharmaceutically acceptable salt, conjugate or complex, thereof, preferably fingolimod HCl,
(b) 0.1-2.0% by weight of a surfactant, preferably an ionic surfactant, more preferably sodium lauryl sulfate,
(c) 70-95% by weight of a NCF sugar alcohol, preferably selected from the group consisting of mannitol, sorbitol, xylitol, sucrose, maltose, and combinations thereof, more preferably mannitol,
(d) 1-10% by weight of a CAF sugar alcohol, preferably selected from the group consisting of maltitol, lactitol, erythritol, isomalt, and combinations thereof, more preferably lactitol,
(e) 0.5-5% by weight of a binder, preferably povidone, more preferably povidone K30, and
(f) 0.1-3% by weight of a lubricant, preferably sodium stearyl fumarate or magnesium stearate, more preferably magnesium stearate,
based on the total weight of the tablet.

As an especially preferred embodiment, the present invention provides an orally disintegrating tablet comprising:
(a) 0.1-1.0% by weight of fingolimod or a pharmaceutically acceptable salt, conjugate or complex thereof, preferably fingolimod HCl,
(b) 1.0-10.0% by weight of a solubilizing agent, preferably a cyclodextrin or a derivative thereof, more preferably hydroxypropyl-beta-cyclodextrin,
(c) 60-95% by weight of a NCF sugar alcohol, preferably selected from the group consisting of mannitol, sorbitol, xylitol, sucrose, maltose, and combinations thereof, more preferably mannitol,
(d) 1-10% by weight of a CAF sugar alcohol, preferably selected from the group consisting of maltitol, lactitol, erythritol, isomalt, and combinations thereof, more preferably lactitol,
(e) 0.5-5% by weight of a binder, preferably povidone, more preferably povidone K30, and
(f) 0.1-3% by weight of a lubricant, preferably sodium stearyl fumarate or magnesium stearate, more preferably magnesium stearate,
based on the total weight of the tablet.

According to the present invention there is also provided a method of treatment of multiple sclerosis in patients in need of such treatment which comprises administering an effective amount of fingolimod or any pharmaceutically acceptable form thereof in the form of the compositions or tablets as described herein.

According to the present invention there is also provided the compositions or tablets described herein for use in the treatment of multiple sclerosis.

According to the present invention there is also provided the use of the compositions or tablets described herein for the manufacture of a medicament for the treatment of multiple sclerosis.

According to the present invention there is also provided a medicament for the treatment of multiple sclerosis comprising the compositions or tablets as described herein.

The term multiple sclerosis (MS) herein encompasses also subtypes of MS, e.g. relapsing-remitting MS (RRMS), chronic progressive MS (CPMS) with its subtypes primary progressive MS (PPMS) and progressive relapsing MS (PRMS), and secondary progressive MS (SPMS).

If not otherwise defined, the test methods referred to herein are to be conducted in accordance to the general chapters of the United States Pharmacopeia (USP) 38 (2015) which are incorporated herein by reference:

The hardness testing is to be conducted using the method and apparatus described in USP 38, General Chapter <1217> with n=4.

The disintegration testing is to be conducted using the method and apparatus described in USP 38 General Chapter <701> basket-rack assembly with n=3.

The friability testing is to be conducted using the method and apparatus described in USP General Chapter <1216> with about 1 gram of tablets being employed.

DESCRIPTION OF THE PREFERRED EMBODIMENTS

The following are provided by way of example only and are by no means intended to be limiting.

Example 1

A rapidly disintegrating fingolimod tablet can be prepared by dissolving fingolimod in an aqueous solution of lactitol. The solution is sprayed onto mannitol and then dried. The resulting product is sifted and blended with other excipients before being compressed into tablets. The tablets should have the following composition:

| | |
|---|---|
| Fingolimod HCl | 0.56 mg* |
| Lactitol | 20 mg |
| Mannitol | 177.44 mg |
| Magnesium Stearate | 2 mg |

*equivalent to 0.5 mg fingolimod

The tablets are placed in a humidity chamber and exposed to 85% relative humidity at 25° C.-30° C. for about 6 hours. After humidification, the tablets are dried at approximately 40° C.-45° C. at 30% relative humidity for about 6 hours.

Example 2

A rapidly disintegrating fingolimod tablet can be prepared by dissolving fingolimod in an aqueous solution of lactitol and mannitol. The solution is sprayed-dried to yield a solid powder. The resulting product is blended with a lubricant and compressed into tablets. The tablets should have the following composition:

| | |
|---|---|
| Fingolimod HCl | 0.56 mg* |
| Lactitol | 20 mg |
| Mannitol | 177.44 mg |
| Magnesium Stearate | 2 mg |

*equivalent to 0.5 mg fingolimod

The tablets are placed in a humidity chamber and exposed to 85% relative humidity at 25° C.-30° C. for about 6 hours. After humidification, the tablets are dried at approximately 40° C.-45° C. at 30% relative humidity for about 6 hours.

The humidified and dried tablets should exhibit a hardness of greater than 2.5 kilopounds, a friability of less than 2% and should disintegrate in less than 60 seconds when placed in a USP disintegration apparatus.

Example 3

A rapidly disintegrating fingolimod tablet can be prepared by lyophilization an aqueous solution of gelatin, lactitol, and mannitol. The solution is transferred to thermoformed blister trays and freeze dried to form tablets. The tablets should have the following composition:

| | |
|---|---|
| Fingolimod HCl | 0.1-5% |
| Lactitol | 5-25% |
| Mannitol | 50-95% |
| Gelatin | 0.5-5% |
| Solubilizing Agent | 0-10% |

The blister trays are freeze-dried at a shelf temperature of −45° C. The resulting product is then heat-dried at a shelf temperature of between 50° C.-55° C. for four hours.

Example 4

A rapidly disintegrating fingolimod tablet can be prepared by the method described in Example 1 wherein the tablet has the following composition:

| | |
|---|---|
| Fingolimod HCl | 0.1-5% |
| MFC Excipient | 2.5-25% |
| NCF Sugar Alcohol | 50-95% |
| Binder | 0-5% |
| Lubricant | 0-2.5% |
| Flavoring Agent | 0-2% |
| Filler | 0-20% |
| Solubilizing Agent | 0-10% |

Example 5

A rapidly disintegrating fingolimod tablet can be prepared by the method described in Example 2 wherein the tablet has the following composition:

| | |
|---|---|
| Fingolimod HCl | 0.1-5% |
| MFC Excipient | 2.5-25% |
| NCF Sugar Alcohol | 50-95% |
| Binder | 0-5% |
| Lubricant | 0-2.5% |
| Flavoring Agent | 0-2% |
| Filler | 0-20% |
| Solubilizing Agent | 0-10% |

Example 6

A rapidly disintegrating fingolimod tablet can be prepared by the method described in Example 3 wherein the tablet has the following composition:

| | |
|---|---|
| Fingolimod HCl | 0.1-5% |
| MFC Excipient | 2.5-25% |
| NCF Sugar Alcohol | 50-95% |
| Binder | 0.1-10% |
| Flavoring Agent | 0-2% |
| Filler | 0-20% |
| Solubilizing Agent | 0-10% |

Example 7

Rapidly disintegrating fingolimod tablets with the following composition were prepared:

| | 7A Mg/tablet [% (w/w)] | 7B Mg/tablet [% (w/w)] |
|---|---|---|
| Mannitol 160C | 188.3 (92.55) | 188.3 (92.55) |
| Fingolimod HCl | 0.6 (0.28) | 0.6 (0.28) |
| Sodium Lauryl Sulfate | 0.6 (0.28) | 0.6 (0.28) |
| Lactitol | 6.0 (2.94) | 6.0 (2.94) |
| Povidone K30 | 4.0 (1.96) | 4.0 (1.96) |
| Sodium Stearyl Fumarate | 4.1 (2.0) | |
| Magnesium Stearate | | 0.602 (0.3) |
| Total | 203.5 (100) | 200.1 (100) |

The above tablets were prepared by dissolving the sodium lauryl sulfate in water. Fingolimod HCl, povidone and lactitol were subsequently added while stirring to create a granulating solution.

The mannitol was added to a top spray fluidized bed granulator. The granulating solution was sprayed onto the mannitol. The resulting drug layered mannitol granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

Example 8

Rapidly disintegrating fingolimod tablets with the following composition were prepared:

| | 8A Mg/tablet [% (w/w)] | 8B Mg/tablet [% (w/w)] |
|---|---|---|
| Mannitol 160C | 184.43 (90.38) | 184.43 (91.94) |
| Fingolimod HCl | 0.56* (0.27) | 0.56* (0.28) |
| Hydroxypropyl-β-Cyclodextrin | 5.0 (2.45) | 5.0 (2.49) |
| Lactitol | 6.0 (2.94) | 6.0 (2.99) |
| Povidone K30 | 4.0 (1.96) | 4.0 (1.99) |
| Sodium Stearyl Fumarate | 4.08 (2.0) | |
| Magnesium Stearate | | 0.60 (0.3) |
| Total | 204.07 (100) | 200.59 (100) |

*equivalent to 0.50 mg fingolimod

The above tablets were prepared by dissolving the hydroxypropyl-β-cyclodextrin in water. Fingolimod HCl, povidone and lactitol were subsequently added while stirring to create a granulating solution.

The mannitol was added to a top spray fluidized bed granulator. The granulating solution was sprayed onto the mannitol. The resulting drug layered mannitol granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

Example 9

Rapidly disintegrating fingolimod tablets with the following composition were prepared:

|  | 9A Mg/tablet [% (w/w)] | 9B Mg/tablet [% (w/w)] |
|---|---|---|
| Mannitol 160C | 188.84 (94.01) | 188.91 (95.63) |
| Fingolimod HCl | 0.56 (0.28) | 0.56 (0.28) |
| Hydroxypropyl methylcellulose E5LV | 0.56* (0.28) | 0.56* (0.28) |
| Lactitol | 4.14 (2.06) | 4.14 (2.10) |
| Povidone K30 | 2.76 (1.37) | 2.76 (1.40) |
| Sodium Stearyl Fumarate | 4.02 (2.0) |  |
| Magnesium Stearate |  | 0.60 (0.31) |
| Total | 200.89 (100) | 197.54 (100) |

*equivalent to 0.50 mg fingolimod

The above tablets were prepared by dissolving the hydroxypropyl methylcellulose E5LV in water. Fingolimod HCl, povidone and lactitol were subsequently added while stirring to create a granulating solution.

The mannitol was added to a top spray fluidized bed granulator. The granulating solution was sprayed onto the mannitol. The resulting drug layered mannitol granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

Example 10

Rapidly disintegrating fingolimod tablets with the following composition were prepared:

|  | 10A Mg/tablet [% (w/w)] | 10B Mg/tablet [% (w/w)] | 10C Mg/tablet [% (w/w)] |
|---|---|---|---|
| Mannitol 160C | 185.7 (92.82) | 185.7 (94.43) | 189.9 (94.94) |
| Fingolimod HCl | 0.56* (0.28) | 0.56* (0.28) | 0.56* (0.28) |
| Lactitol | 5.88 (2.94) | 5.88 (2.99) | 5.37 (2.68) |
| Povidone K30 | 3.92 (1.96) | 3.92 (1.99) | 3.58 (1.79) |
| Sodium Stearyl Fumarate | 4.00 (2.0) |  |  |
| Magnesium Stearate |  | 0.59 (0.3) | 0.60 (0.3) |
| Total | 200.06 (100) | 196.65 (100) | 200.01 (100) |

*equivalent to 0.50 mg fingolimod

The above tablets were prepared by dissolving the lactitol and povidone in water. Fingolimod HCl was subsequently added while stirring to create a granulating solution.

The mannitol was added to a top spray fluidized bed granulator. The granulating solution was sprayed onto the mannitol. The resulting drug layered mannitol granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

The tablets were tested and exhibited the following properties:

|  | 10A Mg/tablet [% (w/w)] | 10B Mg/tablet [% (w/w)] | 10C Mg/tablet [% (w/w)] |
|---|---|---|---|
| Hardness | 8.3N | 7.7N | 38.3N |
| Disintegration time | 21 seconds | 18 seconds | 19 seconds |
| Friability | 5.05% | 12.54% | 0.0% |

The hardness testing was conducted using the method and apparatus described in United States Pharmacopeia 38, (2015) (USP) General Chapter <1217> with n=4.

The disintegration testing was conducted using the method and apparatus described in USP 38 General Chapter <701> basket-rack assembly with n=3.

The friability testing was conducted using the method and apparatus described in USP 38 General Chapter <1216> with about 1 gram of tablets being employed.

Example 11

Rapidly disintegrating fingolimod tablets with the following composition were prepared:

|  | 11A Mg/tablet [% (w/w)] | 11B Mg/tablet [% (w/w)] |
|---|---|---|
| Mannitol 160C | 179.45 (87.93) | 179.45 (89.45) |
| Fingolimod HCl | 0.56* (0.27) | 0.56* (0.28) |
| Hydroxypropyl-β- | 10.00 | 10.00 |

|  | 11A<br>Mg/tablet<br>[% (w/w)] | 11B<br>Mg/tablet<br>[% (w/w)] |
|---|---|---|
| Cyclodextrin | (4.90) | (4.99) |
| Lactitol | 6.0<br>(2.94) | 6.0<br>(2.99) |
| Povidone K30 | 4.0<br>(1.96) | 4.0<br>(1.99) |
| Sodium Stearyl Fumarate | 4.08<br>(2.0) |  |
| Magnesium Stearate |  | 0.60<br>(0.3) |
| Total | 204.09<br>(100) | 200.61<br>(100) |

*equivalent to 0.50 mg fingolimod

The above tablets were prepared by dissolving the hydroxypropyl-β-cyclodextrin in water. Fingolimod HCl, povidone and lactitol were subsequently added while stirring to create a granulating solution.

The mannitol was added to a top spray fluidized bed granulator. The granulating solution was sprayed onto the mannitol. The resulting drug layered mannitol granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

The tablets were tested according to the procedures outlined in Example 10 and exhibited the following properties:

|  | 11A<br>Mg/tablet<br>[% (w/w)] | 11B<br>Mg/tablet<br>[% (w/w)] |
|---|---|---|
| Hardness | 67.1N | 69.0N |
| Disintegration Time | 27 seconds | 19 seconds |
| Friabiltiy | 0.85% | 0.65% |

Example 12

Rapidly disintegrating fingolimod tablets with the following composition were prepared:

|  | 12A<br>Mg/tablet<br>[% (w/w)] | 12B<br>Mg/tablet<br>[% (w/w)] |
|---|---|---|
| Mannitol 160C | 186.12<br>(93.07) | 186.12<br>(93.07) |
| Fingolimod HCl | 0.56*<br>(0.28) | 0.56*<br>(0.28) |
| Sodium Metabisulfate | 0.56<br>(0.28) | 0.56<br>(0.28) |
| Lactitol | 5.25<br>(2.62) | 5.25<br>(2.62) |
| Povidone K30 | 3.50<br>(1.75) | 3.5<br>(1.75) |
| Sodium Stearyl Fumarate | 4.00<br>(2.0) |  |
| Magnesium Stearate |  | 0.60<br>(0.3) |
| Total | 200<br>(100) | 197<br>(100) |

*equivalent to 0.50 mg fingolimod

The above tablets were prepared by dry blending the mannitol, fingolimod HCl and sodium metabisulfate using a geometric technique to form an ordered dry mixture. The ordered dry mixture was added to a top spray fluidized bed granulator and granulated with an aqueous solution of povidone and lactitol. The resulting drug granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

Example 13

Rapidly disintegrating fingolimod tablets with the following composition were prepared:

|  | 13A<br>Mg/tablet<br>[% (w/w)] | 13B<br>Mg/tablet<br>[% (w/w)] |
|---|---|---|
| Mannitol 160C | 186.57<br>(93.29) | 189.9<br>(94.9) |
| Fingolimod HCl | 0.56*<br>(0.28) | 0.56*<br>(0.28) |
| Butylated Hydroxytoluene | 0.10<br>(0.05) | 0.10<br>(0.05) |
| Lactitol | 5.26<br>(2.63) | 5.36<br>(2.68) |
| Povidone K30 | 3.51<br>(1.75) | 3.57<br>(1.79) |
| Sodium Stearyl Fumarate | 4.00<br>(2.0) |  |
| Magnesium Stearate |  | 0.60<br>(0.3) |
| Total | 200<br>(100) | 200<br>(100) |

*equivalent to 0.50 mg fingolimod

The above tablets were prepared by dry blending the mannitol, fingolimod HCl and butylated hydroxytoluene using a geometric technique to form an ordered dry mixture. The ordered dry mixture was added to a top spray fluidized bed granulator and granulated with an aqueous solution of povidone and lactitol. The resulting drug granules were dried and sized, then blended with either the sodium stearyl fumarate or magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

The tablets were tested according to the procedures outlined in Example 10 and exhibited the following properties:

|  | 13A Mg/tablet [% (w/w)] | 13B Mg/tablet [% (w/w)] |
| --- | --- | --- |
| Hardness | 45.4N | 40.7N |
| Disintegration Time | 35 seconds | 15 seconds |
| Friabiltiy | 1.65% | 0.97% |

Example 14

Rapidly disintegrating fingolimod tablets with the following composition were prepared:

|  | 14A Mg/tablet [% (w/w)] | 14B Mg/tablet [% (w/w)] |
| --- | --- | --- |
| Mannitol 160C | 186.6 (94.9) | 189.9 (94.9) |
| Fingolimod HCl | 0.56* (0.28) | 0.56* (0.28) |
| Butylated Hydroxytoluene | 0.10 (0.05) | 0.10 (0.05) |
| Disodium EDTA | 0.05 (0.03) | 0.05 (0.03) |
| Lactitol | 5.26 (2.67) | 5.26 (2.67) |
| Povidone K30 | 3.51 (1.78) | 3.51 (1.78) |
| Magnesium Stearate | 0.60 (0.31) | 0.60 (0.31) |
| Total | 196.6 (100) | 196.6 (100) |

*equivalent to 0.50 mg fingolimod

Tablets 14A were prepared by dry blending the mannitol, fingolimod HCl, butylated hydroxytoluene and disodium EDTA using a geometric technique to form an ordered dry mixture. The ordered dry mixture was added to a top spray fluidized bed granulator and granulated with an aqueous solution of povidone and lactitol. The resulting drug granules were dried and sized, then blended with magnesium stearate, and compressed into 9 mm round tablets.

Tablets 14B were prepared by dry blending the mannitol, fingolimod HCl and butylated hydroxytoluene using a geometric technique to form an ordered dry mixture. The ordered dry mixture was added to a top spray fluidized bed granulator and granulated with an aqueous solution of povidone and lactitol. The resulting drug granules were dried and sized. The disodium EDTA was dissolved in water and mixed with magnesium stearate to form magnesium stearate granules. The magnesium stearate granules were dried at 105° C. for ten minutes, cooled then blended, and the dried and sized drug granules were compressed into 9 mm round tablets The tablets were placed in a humidity chamber and exposed to 75% relative humidity at 30° C. for about 0.5 hours. After humidification, the tablets were dried at approximately 30° C. at 30% relative humidity for about 2 hours.

Example 15

Rapidly disintegrating fingolimod tablets prepared in Examples 7-14 were packaged in aluminum foil pouch and heat sealed. The sealed pouches were stored at 60° C. and 60% relative humidity. After 14 days the tablets were tested using a validated HPLC methodology and impurity were reported as follows:

|  | Initial | | 7 Days | | 14 Days | |
| --- | --- | --- | --- | --- | --- | --- |
| Example | Max Single Impurity | Total Impurities | Max Single Impurity | Total Impurities | Max Single Impurity | Total Impurities |
| 7A | ND | 0.0% | 0.13% | 0.19% | 0.10% | 0.17% |
| 7B | ND | 0.0% | 0.06% | 0.18% | 0.16% | 0.39% |
| 8A | 0.07% | 0.07% | 0.25% | 1.51% | 0.42% | 2.78% |
| 8B | 0.08% | 0.08% | 0.20% | 1.64% | 0.39% | 3.0% |
| 9A | ND | 0.0% | 2.00% | 7.18% | | |
| 9B | ND | 0.0% | 0.67% | 5.74% | | |
| 10A | 0.19% | 0.38% | 0.73% | 3.08% | 0.84% | 3.05% |
| 10B | 0.18% | 0.36% | 0.65% | 11.45% | 4.54% | 24.52% |
| 10C | ND | 0.0% | 0.31% | 2.23% | 0.81% | 4.29% |
| 11A | ND | 0.0% | 0.25% | 1.02% | 0.45% | 2.43% |
| 11B | ND | 0.0% | 0.17% | 0.64% | 0.25% | 1.20% |
| 12A | ND | 0.0% | 0.11% | 0.27% | 0.31% | 1.24% |
| 12B | ND | 0.0% | 0.11% | 0.17% | 0.11% | 0.54% |
| 13A | ND | 0.0% | 0.55% | 1.28% | 0.91% | 2.75% |
| 13B | ND | 0.0% | 0.21% | 0.71% | 0.49% | 1.34% |
| 14A | ND | 0.0% | 0.27% | 0.89% | 0.33% | 1.01% |
| 14B | ND | 0.0% | 0.22% | 0.65% | 0.35% | 1.76% |

Example 16

Rapidly disintegrating fingolimod tablets with the following composition were prepared:

|  | Mg/tablet [% (w/w)] |
| --- | --- |
| Mannitol 160C | 178.84 (89.42) |
| Fingolimod HCl | 0.56* (0.28) |
| Hydroxypropyl-β-Cyclodextrin | 10.00 (5.00) |
| Lactitol | 6.0 (3.00) |
| Povidone K30 | 4.0 (2.00) |
| Magnesium Stearate | 0.60 (0.30) |
| Total | 200.0 (100) |

*equivalent to 0.50 mg fingolimod

The above tablets were prepared by dissolving 75 g of hydroxypropyl-β-cyclodextrin in 300 g of purified water. 4.2 g of fingolimod HCl, 30 g of povidone and 45 g of lactitol were subsequently added to the cyclodextrin aqueous solution while stirring to create a granulating solution.

1,341 g of mannitol was added to a top spray fluidized bed granulator. The granulating solution was sprayed onto the mannitol. The resulting drug layered mannitol granules were dried and sized, then blended with 5 g of magnesium stearate, and compressed into 9 mm round tablets.

The tablets were placed in a humidity chamber and exposed to 75% relative humidity at 30° C. for about 0.5 hours. After humidification, the tablets were dried at approximately 30° C. at 30% relative humidity for about 2 hours.

The humidified and dried tablets were tested according to the procedures outlined in Example 10 and exhibited the following properties:

| Hardness | 69.8N |
|---|---|
| Disintegration Time | 20-26 seconds |
| Friability | 0.38% |

The humidified and dried tablets also exhibited the following mean (n=3) in vitro dissolution profile when tested using a USP Type II (paddles) at 75 rpms in 500 mL of 0.1N HCl with 0.2% sodium lauryl sulfate and 37° C.:

| Time (min) | | | | |
|---|---|---|---|---|
| 5 | 10 | 15 | 20 | 30 |
| % 85 | 98 | 99 | 99 | 100 |

The humidified and dried tablets were packaged in aluminum blister card and stored at 60° C. and 60% relative humidity. After 14 days the tablets were tested using an HPLC methodology and the impurity profile was reported as follows:

| IMP RRT | Initial | 7 Days | 14 Days |
|---|---|---|---|
| 0.92 | ND | 0.34 | 0.72 |
| 1.05 | ND | 0.18 | 0.39 |
| 1.07 | ND | 0.09 | 0.14 |
| 1.14 | ND | <0.05 | 0.15 |
| 1.18 | ND | 0.47 | 0.94 |
| 1.35 | ND | ND | 0.09 |
| 1.50 | ND | 0.17 | 0.25 |
| Total | ND | 1.25 | 2.68 |

ND = Not Detected

The humidified and dried tablets packaged in aluminum blister card were also stored at 40° C. and 75% relative humidity. After one month the tablets were tested using an HPLC methodology and the impurity profile was reported as follows:

| IMP RRT | Initial | 1 Month |
|---|---|---|
| 0.92 | ND | 0.07 |
| 1.140 | ND | 0.05 |
| Total | ND | 0.12 |

ND = Not Detected

Example 17

Rapidly disintegrating fingolimod tablets with the following composition were prepared:

| | Mg/tablet (% w/w) |
|---|---|
| Granulation 1 | |
| Granulation Solution A | |
| Purified Water | N/A* |
| Fingolimod HCl | 0.56 (0.28) |
| Sodium Lauryl Sulfate | 0.56 (0.28) |
| Povidone (Plasdone K29/32) | 0.56 (0.28) |
| Granulation Solution B | |
| Purified Water | N/A* |
| Lactitol Monohydrate | 3.00 (1.50) |
| Povidone (Plasdone K29/32) | 2.00 (1.00) |
| Mannitol (Pearlitol 160C) | 93.00 (46.50) |
| Granulation 2 | |
| Granulation Solution C | |
| Purified Water | N/A* |
| Lactitol Monohydrate | 3.00 (1.50) |
| Povidone (Plasdone K29/32) | 2.00 (1.00) |
| Mannitol (Pearlitol 160C) | 94.70 (47.35) |
| Blend | |
| Magnesium Stearate | 0.60 (0.30) |

The above tablets were as follows.
Granulation 1 was prepared by:
dissolving 8.4 g of fingolimod HCl in 160 g of purified water to create a fingolimod solution;
dissolving 7.8 g of povidone in 160 g of purified water while mixing and add 8.4 g of sodium lauryl sulfate to create a binder solution;
pumping the binder solution slowly into the fingolimod solution, homogenizing the combined solution and add an additional 180 g of purified water; in a separate container 0.6 g of povidone is dissolved in 60 g of purified water and the resulting povidone solution is added to the homogenized fingolimod/binder solution to create granulation solution A;
dissolving 45 g of lactitol and 30 g of povidone in 299 g of purified water to create granulation solution B;
1,395 g of mannitol was added to a top spray fluidized bed granulator and granulation solution A and then granulation solution B were sprayed onto the mannitol. The resulting drug layered mannitol granules were dried and sized.
Granulation 2 was prepared by:
dissolving 45 g of lactitol and 30 g of povidone in 600 g of purified water to create granulation solution C;
1,421 g of mannitol was added to a top spray fluidized bed granulator and granulation solution C was sprayed onto the mannitol. The resulting granules were dried and sized.

Granulation 1 and Granulation 2 were combined and blended with 9 g of magnesium stearate and resulting blend was compressed into 9 mm round tablets.

The tablets were placed in a humidity chamber and exposed to 75% relative humidity at 30° C. for about 1 hours. After humidification, the tablets were dried at approximately 30° C. at 30% relative humidity for about 2 hours.

The humidified and dried tablets were tested according to the procedures outlined in Example 10 and exhibited the following properties:

| | |
|---|---|
| Hardness | 58.0N |
| Disintegration Time | 55-65 seconds |
| Friability | 0.03% |

The humidified and dried tablets also exhibited the following mean (n=3) in vitro dissolution profile when tested using a USP Type II (paddle) at 75 rpms in 500 mL of 0.1N HCl with 0.2% sodium lauryl sulfate and 37° C.:

| | Time (min) | | | | |
|---|---|---|---|---|---|
| | 5 | 10 | 15 | 20 | 30 |
| % | 82 | 90 | 91 | 91 | 91 |

The humidified and dried tablets were packaged in aluminum blister card and stored at 60° C. and 60% relative humidity. After 14 days the tablets were tested using an HPLC methodology and the impurity profile was reported as follows:

| IMP RRT | Initial | 7 Days | 14 Days |
|---|---|---|---|
| 0.91 | ND | 0.09 | 0.15 |
| Total | ND | 0.09 | 0.15 |

ND = Not Detected

The humidified and dried tablets packaged in aluminum blister cards were also stored at 40° C. and 75% relative humidity. After one month the tablets were tested using a validated HPLC methodology and the impurity profile was reported as follows:

| IMP RRT | Initial | 1 Month |
|---|---|---|
| 0.91 | ND | ND |
| Total | ND | ND |

ND = Not Detected

Example 18

The tablets from Examples 16 and 17 were administered to healthy adult male and non-pregnant human volunteer subjects, in a single-center, single-dose, randomized, three treatment, parallel study. Twenty-four subjects completed the study. Each subject received a single dose of the following treatments under fasted conditions:

Treatment 1 (Test Product 1): 8 subjects were administered three (3) tablets of Example 16 wherein the first of the three tablets was placed on the subject's tongue. The subject was instructed to allow the first tablet to remain in the oral cavity for 30 seconds, then drink 50 mL of water. This procedure was repeated sequentially for the second and third tablets so all three tablets were administered in about 2 minutes or less;

Treatment 2 (Test Product 2): 8 subjects were administered three (3) tablets of Example 17 wherein the first of the three tablets was placed on the subject's tongue. The subject was instructed to allow the first tablet to remain in the oral cavity for 30 seconds, then drink 50 mL of water. This procedure was repeated sequentially for the second and third tablets so all three tablets were administered in about 2 minutes or less;

Treatment 3 (Reference Product): 8 subjects were administered three (3) commercially available 0.5 mg GILENYA® capsules with 200 mL of water.

An 8 ml blood sample was collected pre-dose and 4 ml blood samples were collected 2, 4, 6, 8, 10, 12, 14, 16, 20, 24, 30, 36, 48, 60, 72, 96 and 120 hours post-dose with EDTA tubes and analyzed for fingolimod concentrations by a LC/MS/MS method. The results from this study are as follows:

Treatment 1 (Test Product 1—Example 16)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 103 | 152.6 | 360.5 | 1.734 | 36.00 | 203.85 | 132.19 | 0.8385 |
| 106 | 105.1 | 162.2 | 1.368 | 30.00 | 113.79 | 97.14 | 0.9957 |
| 111 | 140.3 | 409.2 | 1.567 | 48.00 | 273.44 | 184.15 | 0.6093 |
| 114 | 151.7 | 305.5 | 1.932 | 12.00 | 165.05 | 105.72 | 0.8683 |
| 116 | 128.4 | 235.2 | 1.432 | 16.00 | 150.07 | 98.29 | 0.9838 |
| 117 | 102.5 | 197.4 | 1.385 | 30.00 | 158.19 | 102.89 | 0.8533 |
| 123 | 96.6 | 148.4 | 1.209 | 30.00 | 112.17 | 65.68 | 0.9999 |
| 126 | 140.1 | 229.3 | 1.612 | 30.00 | 123.69 | 74.93 | 0.9995 |
| Mean | 127.2 | 255.9 | 1.530 | 29.00 | 162.53 | 103.87 | 0.8935 |
| SD | 22.7 | 93.9 | 0.230 | 11.16 | 54.26 | 39.51 | 0.1348 |
| CV(%) | 17.9 | 36.7 | 15.1 | 38.5 | 33.4 | 38.0 | 15.1 |
| median | 134.2 | 232.2 | 1.500 | 30.00 | 154.13 | 100.59 | 0.9260 |

Treatment 2 (Test Product 2—Example 17)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 104 | 116.0 | 254.6 | 1.304 | 36.00 | 191.49 | 126.83 | 0.9313 |
| 107 | 120.7 | 235.1 | 1.355 | 30.00 | 163.42 | 107.51 | 0.8293 |
| 110 | 128.4 | 242.4 | 1.633 | 12.00 | 157.42 | 105.58 | 0.9268 |
| 113 | 169.7 | 428.2 | 1.828 | 14.00 | 224.82 | 148.29 | 0.8844 |
| 118 | 106.3 | 331.5 | 1.076 | 30.00 | 281.42 | 184.04 | 0.7840 |
| 119 | 119.3 | 224.0 | 1.571 | 12.00 | 160.97 | 112.50 | 0.7897 |
| 121 | 82.7 | 170.5 | 0.973 | 30.00 | 177.95 | 118.02 | 0.9034 |
| 124 | 144.5 | 655.4 | 1.574 | 6.00 | 474.73 | 327.21 | 0.622 |
| Mean | 123.5 | 317.7 | 1.414 | 21.25 | 229.03 | 153.75 | 0.8339 |
| SD | 25.7 | 157.4 | 0.291 | 11.36 | 107.71 | 74.83 | 0.1034 |
| CV(%) | 20.9 | 49.5 | 20.6 | 53.5 | 47.0 | 48.7 | 12.4 |
| median | 120.0 | 248.5 | 1.463 | 22.00 | 184.72 | 122.43 | 0.8568 |

Treatment 3 (Reference Product)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 101 | 141.0 | 284.7 | 1.714 | 30.00 | 174.66 | 118.98 | 0.9825 |
| 102 | 151.7 | 323.5 | 2.015 | 14.00 | 170.23 | 103.65 | 0.5470 |
| 105 | 127.5 | 433.1 | 1.495 | 36.00 | 335.49 | 229.44 | 0.8827 |
| 108 | 111.1 | 193.1 | 1.449 | 30.00 | 136.37 | 88.30 | 0.9102 |

-continued

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 112 | 133.9 | 223.4 | 1.628 | 12.00 | 128.51 | 80.96 | 0.9858 |
| 115 | 111.9 | 252.8 | 1.281 | 30.00 | 193.22 | 125.18 | 0.8816 |
| 120 | 101.7 | 222.7 | 1.513 | 20.00 | 192.44 | 130.05 | 0.9111 |
| 122 | 123.7 | 616.5 | 1.501 | 30.00 | 541.99 | 376.49 | 0.9633 |
| Mean | 125.3 | 318.7 | 1.575 | 25.25 | 234.11 | 156.63 | 0.8830 |
| SD | 16.8 | 142.1 | 0.218 | 8.75 | 139.79 | 99.97 | 0.1421 |
| CV(%) | 13.4 | 44.6 | 13.9 | 34.6 | 59.7 | 63.8 | 16.1 |
| median | 125.6 | 268.8 | 1.507 | 30.00 | 183.55 | 122.08 | 0.9106 |

Log Transformed Ratio (Test Product 1: Reference)

| | Point Estimate | 90% Confidence Interval | | P-value |
|---|---|---|---|---|
| | | Lower Bound | Upper Bound | |
| Ln ($AUC_{0-t}$) | 1.0078 | 87.41 | 116.19 | 0.925 |
| Ln ($AUC_{0-\infty}$) | 0.8143 | 58.41 | 113.53 | 0.295 |
| Ln ($C_{max}$) | 0.9699 | 85.65 | 109.85 | 0.672 |
| MRT | 0.6942 | 29.54 | 109.30 | 0.198 |
| $T_{1/2}$ | 0.6632 | 23.59 | 109.04 | 0.187 |
| $T_{max}$ | 1.1485 | | | 0.564 |

Log Transformed Ratio (Test Product 2: Reference)

| | Point Estimate | 90% Confidence Interval | | P-value |
|---|---|---|---|---|
| | | Lower Bound | Upper Bound | |
| Ln ($AUC_{0-t}$) | 0.9740 | 83.34 | 113.84 | 0.771 |
| Ln ($AUC_{0-\infty}$) | 0.9818 | 68.52 | 140.69 | 0.930 |
| Ln ($C_{max}$) | 0.8876 | 75.75 | 104.01 | 0.207 |
| MRT | 0.9783 | 50.90 | 144.76 | 0.936 |
| $T_{1/2}$ | 0.9816 | 48.52 | 147.79 | 0.949 |
| $T_{max}$ | 0.8416 | | | 0.495 |

Example 19

The tablets from Examples 16 and 17 were administered to healthy adult male and non-pregnant human volunteer subjects, in a single-center, single-dose, randomized, three treatment, parallel study. Twenty-four subjects were enrolled. Each subject received a single dose of the following treatments under fed conditions:

Treatment 1 (Test Product 1): 8 subjects were administered three (3) tablets of Example 16 wherein the first of the three tablets was placed on the subject's tongue. The subject was instructed to allow the first tablet to remain in the oral cavity for 30 seconds, then drink 50 mL of water. This procedure was repeated sequentially for the second and third tablets so all three tablets were administered in about 2 minutes or less;

Treatment 2 (Test Product 2): 7 subjects were administered three (3) tablets of Example 17 wherein the first of the three tablets was placed on the subject's tongue. The subject was instructed to allow the first tablet to remain in the oral cavity for 30 seconds, then drink 50 mL of water. This procedure was repeated sequentially for the second and third tablets so all three tablets were administered in about 2 minutes or less;

Treatment 3 (Reference Product): 9 subjects were administered three (3) commercially available 0.5 mg GILENYA® capsules with 200 mL of water.

An 8 ml blood sample was collected pre-dose and 4 ml blood samples were collected 2, 4, 6, 8, 10, 12, 14, 16, 20, 24, 30, 36, 48, 60, 72, 96 and 120 hours post-dose with EDTA tubes and analyzed for fingolimod concentrations by a LC/MS/MS method. The results from this study are as follows:

Treatment 1 (Test Product 1—Example 16)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 101 | 154.5 | 347.0 | 1.723 | 30.00 | 193.25 | 125.72 | 0.9549 |
| 106 | 125.5 | 223.8 | 1.494 | 30.00 | 147.97 | 102.01 | 0.9237 |
| 110 | 132.9 | 294.2 | 1.411 | 16.00 | 190.10 | 124.10 | 0.9690 |
| 112 | 140.5 | 234.2 | 1.889 | 30.00 | 129.35 | 85.09 | 0.9762 |
| 113 | 146.8 | 280.0 | 1.670 | 8.00 | 152.03 | 94.10 | 0.9533 |
| 115 | 88.7 | 148.0 | 1.075 | 30.00 | 117.72 | 60.75 | 0.8783 |
| 120 | 167.8 | 361.8 | 2.109 | 30.00 | 193.56 | 134.07 | 0.9746 |
| 121 | 121.0 | 297.0 | 1.410 | 30.00 | 202.63 | 125.46 | 0.7138 |
| Mean | 134.7 | 273.2 | 1.598 | 25.50 | 165.83 | 106.41 | 0.9180 |
| SD | 24.1 | 69.7 | 0.321 | 8.60 | 32.99 | 25.42 | 0.0887 |
| CV(%) | 17.9 | 25.5 | 20.1 | 33.7 | 19.9 | 23.9 | 9.7 |
| median | 136.7 | 287.1 | 1.582 | 30.00 | 171.07 | 113.06 | 0.9541 |

Treatment 2 (Test Product 2—Example 17)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 102 | 116.6 | 181.0 | 1.286 | 36.00 | 113.71 | 69.84 | 0.9665 |
| 107 | 129.9 | 546.8 | 1.428 | 30.00 | 438.42 | 302.52 | 0.9511 |
| 109 | 140.3 | 231.0 | 1.752 | 30.00 | 126.49 | 80.28 | 0.9709 |
| 117 | 92.5 | 186.2 | 1.161 | 30.00 | 170.44 | 113.38 | 0.9904 |
| 118 | 127.8 | 234.8 | 1.492 | 36.00 | 148.75 | 98.43 | 0.9191 |
| 122 | 132.6 | 270.1 | 1.630 | 30.00 | 175.54 | 117.78 | 0.9852 |
| 123 | 142.9 | 259.5 | 1.591 | 30.00 | 146.18 | 91.64 | 0.8481 |
| Mean | 126.1 | 272.8 | 1.477 | 31.71 | 188.50 | 124.84 | 0.9473 |
| SD | 17.2 | 125.4 | 0.205 | 2.93 | 112.37 | 80.17 | 0.0498 |
| CV(%) | 13.6 | 46.0 | 13.8 | 9.2 | 59.6 | 64.2 | 5.3 |
| median | 129.9 | 234.8 | 1.492 | 30.00 | 148.75 | 98.43 | 0.9665 |

Treatment 3 (Reference Product)

| subject | $AUC_{0-t}$ (ng * h/ mL) | $AUC_{0-\infty}$ (ng * h/ mL) | $C_{max}$ (ng/mL) | $T_{max}$ (h) | MRT (h) | $T_{1/2}$ (h) | RSQ |
|---|---|---|---|---|---|---|---|
| 103 | 134.7 | 211.9 | 1.507 | 30.00 | 117.55 | 71.42 | 0.9509 |
| 104 | 191.5 | 373.1 | 2.042 | 36.00 | 158.49 | 98.70 | 0.9903 |
| 105 | 131.0 | 334.8 | 1.482 | 30.00 | 233.16 | 155.72 | 0.9996 |
| 108 | 158.1 | 226.7 | 1.735 | 36.00 | 100.25 | 47.35 | 1.0000 |
| 111 | 134.4 | 201.3 | 1.416 | 36.00 | 105.87 | 52.60 | 1.0000 |
| 114 | 141.2 | 235.2 | 1.503 | 72.00 | 128.11 | 76.30 | 1.0000 |
| 119 | 135.3 | 340.6 | 1.662 | 30.00 | 209.01 | 129.63 | 1.0000 |
| 124 | 105.4 | 152.9 | 1.463 | 30.00 | 102.91 | 58.11 | 0.9958 |
| 125 | 139.2 | 289.4 | 1.640 | 30.00 | 171.41 | 107.68 | 0.9388 |
| Mean | 141.2 | 262.9 | 1.606 | 36.67 | 147.42 | 88.61 | 0.9862 |
| SD | 23.3 | 74.7 | 0.195 | 13.56 | 48.79 | 37.13 | 0.0238 |
| CV(%) | 16.5 | 28.4 | 12.1 | 37.0 | 33.1 | 41.9 | 2.4 |
| median | 135.3 | 235.2 | 1.507 | 30.00 | 128.11 | 76.30 | 0.9996 |

Log Transformed Ratio (Test Product 1: Reference)

| | Point Estimate | 90% Confidence Interval | | P-value |
|---|---|---|---|---|
| | | Lower Bound | Upper Bound | |
| Ln ($AUC_{0-t}$) | 0.9501 | 81.74 | 110.44 | 0.560 |
| Ln ($AUC_{0-\infty}$) | 1.0438 | 81.47 | 133.73 | 0.766 |

-continued

Log Transformed Ratio (Test Product 1: Reference)

|  | | 90% Confidence Interval | |  |
| --- | --- | --- | --- | --- |
|  | Point Estimate | Lower Bound | Upper Bound | P-value |
| Ln ($C_{max}$) | 0.9828 | 85.42 | 113.08 | 0.831 |
| MRT | 1.1249561 | 88.13 | 136.84 | 0.383 |
| $T_{1/2}$ | 1.2008 | 89.13 | 151.04 | 0.273 |
| $T_{max}$ | 0.6955 |  |  | 0.049 |

Log Transformed Ratio (Test Product 2: Reference)

|  | | 90% Confidence Interval | |  |
| --- | --- | --- | --- | --- |
|  | Point Estimate | Lower Bound | Upper Bound | P-value |
| Ln ($AUC_{0-t}$) | 0.8954 | 78.05 | 102.72 | 0.178 |
| Ln ($AUC_{0-\infty}$) | 1.0069 | 75.24 | 134.75 | 0.968 |
| Ln ($C_{max}$) | 0.9177 | 81.97 | 102.74 | 0.202 |
| MRT | 1.2787 | 78.33 | 177.41 | 0.339 |
| $T_{1/2}$ | 1.4088 | 81.28 | 200.48 | 0.247 |
| $T_{max}$ | 0.8649 |  |  | 0.560 |

About 24% of the patients in the fasted and fed studies reported a slight bitter taste when administered the tablets of Example 16 while 100% of the patients in the studies reported no bitterness when administered the tablets of Example 17.

Example 20

Rapidly disintegrating fingolimod tablets with the following composition can also be prepared by the method described in Example 17:

|  | Mg/tablet (% w/w) |
| --- | --- |
| Granulation 1 | |
| Granulation Solution A | |
| Purified Water | N/A* |
| Fingolimod HCl | 0.56 (0.28) |
| Sodium Lauryl Sulfate | 0.56 (0.28) |
| Povidone (Plasdone K29/32) | 0.58 (0.29) |
| Granulation Solution B | |
| Purified Water | N/A* |
| Lactitol Monohydrate | 3.00 (1.50) |
| Povidone (Plasdone K29/32) | 2.00 (1.00) |
| Mannitol (Pearlitol 160C) | 93.00 (46.50) |
| Granulation 2 | |
| Granulation Solution C | |
| Purified Water | N/A* |
| Lactitol Monohydrate | 3.00 (1.50) |

-continued

|  | Mg/tablet (% w/w) |
| --- | --- |
| Povidone (Plasdone K29/32) | 2.00 (1.00) |
| Mannitol (Pearlitol 160C) | 94.70 (47.35) |
| Blend | |
| Magnesium Stearate | 0.60 (0.30) |

Example 21

A sodium lauryl sulfate solution was prepared by dissolving 1.00 g of sodium lauryl sulfate in 20 mL of water. A fingolimod HCl solution was prepared by dissolving 1.00 g of fingolimod HCl in 20 mL of water. Subsequently, the sodium lauryl sulfate solution was slowly added to the fingolimod HCl solution and the resulting solution was stirred for 30 minutes. It was observed that a white dispersion/precipitate was formed. The resulted suspension was filtered and washed with water to isolate the white solid. The white solid was dried in a vacuum oven at 35-38° C. for 5 hours.

The melting point of the white solid was 124-126° C.

The solubility of the white solid in different medium was tested by an HPLC method and results was summarized in table below:

| Medium | Solubility |
| --- | --- |
| Water | 0.82 μg/mL |
| 0.1N HCl | 1.75 μg/mL |
| pH 4.5 50 mM Acetate Buffer Solution | 1.97 μg/mL |
| pH 6.8 50 mM Phosphate Buffer Solution | 1.11 μg/mL |

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A solid orally disintegrating tablet comprising:
    (a) at least one pharmaceutically acceptable excipient, and
    (b) an amount of 0.1 mg to 1.0 mg of a fingolimod lauryl sulfate salt, conjugate or complex wherein the fingolimod lauryl sulfate salt, conjugate or complex is formed by: i) dissolving fingolimod or a pharmaceutically acceptable salt thereof in a suitable solvent; ii) dissolving an anionic lauryl sulfate or salt thereof in a suitable solvent; iii) allowing the dissolved fingolimod and dissolved lauryl sulfate to react and form the fingolimod lauryl sulfate salt, conjugate or complex; and iv) removing the solvent, wherein said tablet disintegrates when tested using a USP Disintegration apparatus in less than 2.5 minutes;

wherein said tablet contains about 2.0% or less of any individual fingolimod degradation product and a total amount of fingolimod degradation products of about 2.5% or less when the solid pharmaceutical dosage form is stored in a sealed bottle or aluminum foil pouch at approximately 40° C. and approximately 75% relative humidity for one month, and wherein, following a single dose administration of said tablet under fasting conditions, the time to maximum fingolimod concentration (Tmax) is about 8 to about 40 hours, the dose adjusted maximum fingolimod concentration ($C_{max/dose}$) is about 0.50 to about 2.0 ng/ml/mg and the dose adjusted area under the plasma concentration ($AUC_{0-\infty/dose}$) is about 100 to about 300 ng·hr/ml/mg;

wherein the fingolimod lauryl sulfate salt, conjugate or complex exhibits a melting point of about 124-126° C.

2. The solid orally disintegrating tablet as defined in claim 1 wherein the at least one pharmaceutically acceptable excipient is selected from the group consisting of lubricants, fillers, binders, disintegrants, glidants, solubilizing agents, flavoring agents, gas producing agents, pH adjusting agents, antioxidants or mixtures of the foregoing.

3. The solid orally disintegrating tablet as defined in claim 2 wherein the at least one pharmaceutically acceptable excipient comprises a binder.

4. The solid orally disintegrating tablet as defined in claim 2 wherein the at least one pharmaceutically acceptable excipient is a filler.

5. The solid orally disintegrating tablet as defined in claim 4 wherein the filler is a sugar alcohol.

6. The solid orally disintegrating tablet as defined in claim 1 wherein the fingolimod lauryl sulfate salt, conjugate or complex is formed by reacting the dissolved fingolimod with the dissolved anionic lauryl sulfate or salt thereof in a ratio of about 1 mole of the fingolimod to about 0.75 moles to about 2 moles of the anionic lauryl sulfate.

7. The solid orally disintegrating tablet as defined in claim 1 wherein the fingolimod lauryl sulfate salt, conjugate or complex is formed by reacting the dissolved fingolimod with the dissolved anionic lauryl sulfate or salt thereof in a ratio of about 1 mole of the fingolimod to about 0.85 moles to about 1.5 moles of the anionic lauryl sulfate.

8. The solid orally disintegrating tablet as defined in claim 1 wherein the fingolimod of (b)(i) is fingolimod hydrochloride and the anionic lauryl sulfate of (b)(ii) is sodium lauryl sulfate.

9. The solid orally disintegrating tablet as defined in claim 1 wherein the fingolimod lauryl sulfate salt, conjugate or complex is formed by: i) dissolving fingolimod or a pharmaceutically acceptable salt thereof in a suitable solvent to form a first solution; ii) dissolving an anionic lauryl sulfate or salt thereof in a suitable solvent to form a second solution; iii) allowing the dissolved fingolimod and dissolved lauryl sulfate to react and form the fingolimod lauryl sulfate salt, conjugate or complex; and iv) removing the solvent;

wherein the first solution, second solution, or first and second solution further comprises a pharmaceutically acceptable excipient selected from the group consisting of fillers, binders, disintegrants, or mixtures of the foregoing.

10. The solid orally disintegrating tablet as defined in claim 9 wherein the pharmaceutically acceptable excipient of the first solution, second solution, or first and second solution is a binder.

11. The solid orally disintegrating tablet as defined in claim 9 wherein the pharmaceutically acceptable excipient of the first solution, second solution, or first and second solution is a filler.

12. The solid orally disintegrating tablet as defined in claim 11 wherein the filler is a sugar alcohol.

13. The solid orally disintegrating tablet as defined in claim 1 wherein following a single dose administration of the tablet under fasting conditions, the time to maximum fingolimod concentration ($T_{max}$) is about 10 to about 35 hours, the dose adjusted maximum fingolimod concentration ($C_{max/dose}$) is about 0.55 to about 1.5 ng/ml/mg and the dose adjusted area under the plasma concentration ($AUC_{0-\infty/dose}$) is about 125 to about 275 ng·hr/ml/mg.

14. The solid orally disintegrating tablet as defined in claim 13 wherein following a single dose administration of the tablet under fasting conditions, the time to maximum fingolimod concentration ($T_{max}$) is about 12 to about 30 hours, the dose adjusted maximum fingolimod concentration ($C_{max/dose}$) is about 0.60 to about 1.25 ng/ml/mg and the dose adjusted area under the plasma concentration ($AUC_{0-\infty/dose}$) is about 150 to about 250 ng·hr/ml/mg.

15. The solid orally disintegrating tablet as defined in claim 1 wherein the amount of fingolimod is about 0.5 mg.

16. The solid orally disintegrating tablet as defined in claim 1 wherein said tablet disintegrates when tested using a USP Disintegration apparatus in less than 2.0 minutes.

17. The solid orally disintegrating tablet as defined in claim 1 wherein said tablet disintegrates when tested using a USP Disintegration apparatus in less than 1.5 minutes.

18. The solid orally disintegrating tablet as defined in claim 1 wherein the fingolimod lauryl sulfate salt, conjugate or complex is a fingolimod lauryl sulfate salt.

* * * * *